United States Patent
Nelson

(10) Patent No.: US 7,105,654 B1
(45) Date of Patent: Sep. 12, 2006

(54) **ETHYLENE RECEPTOR GENE FROM *GLYCINE MAX* AND ITS USE**

(75) Inventor: Donald E. Nelson, Stonington, CT (US)

(73) Assignee: Monsanto Technology LLC, St. Louis, MO (US)

( * ) Notice: Subject to any disclaimer, the term of this patent is extended or adjusted under 35 U.S.C. 154(b) by 189 days.

(21) Appl. No.: 10/325,034

(22) Filed: Dec. 20, 2002

Related U.S. Application Data

(60) Provisional application No. 60/345,960, filed on Jan. 2, 2002.

(51) Int. Cl.
 *C07H 21/04* (2006.01)

(52) U.S. Cl. .................... 536/23.6; 536/23.1; 435/419; 800/283; 800/287; 800/298; 800/306; 800/310; 800/312; 800/313; 800/314; 800/315; 800/317.2; 800/317.4; 800/320

(58) Field of Classification Search ............... 536/23.1, 536/23.6; 435/419; 800/278, 283, 287, 800/298, 306, 312, 310, 313, 314, 315, 317.2, 800/317.4, 320
See application file for complete search history.

(56) References Cited

U.S. PATENT DOCUMENTS 6,294,716 B1 * 9/2001 Meyerowitz et al. .... 800/317.4

* cited by examiner

*Primary Examiner*—Russell P. Kallis
(74) *Attorney, Agent, or Firm*—Thomas E. Kelley

(57) ABSTRACT

The present invention relates to an isolated nucleic acid sequence from a soybean plant (*Glycine max*) encoding an ethylene receptor polypeptide. The present invention also relates to methods for reducing an ethylene-induced abscission of reproductive structures by producing a transformed plant containing a modified ethylene receptor gene. The transformed plants herein produced demonstrate yield enhancement at their maturity.

13 Claims, 6 Drawing Sheets

SEQUENCE LISTING

<160> NUMBER OF SEQ ID NOS: 13

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:
      synthetic primer

<400> SEQUENCE: 1
gcttttattg ttctctatgg agcaactcat ttc                           33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:
      synthetic primer

<400> SEQUENCE: 2
gaaatgagtt gctccataga gaacaataaa agc                           33

<210> SEQ ID NO 3
<211> LENGTH: 1911
<212> TYPE: DNA
<213> ORGANISM: Glycine max

<400> SEQUENCE: 3
atgatggaat cctgtgattg tatagacaca cagtatcctc cagatgaact tctcgtaaag    60
tatcagtata tctcggatgt gctaattgct cttgcctatt tttctattcc cgtggagctc   120
atctattttg ttcagaagtc tgctttcttt ccatatagat gggtgcttat gcagtttggt   180
gcttttattg ttctctgtgg agcaactcat ttcataaacc tgtggacatt ctccccacac   240
tctaaggctg ttgctgttgt catgacgatt gccaaagtgt cgtgtgctat tgtgtcatgt   300
gcgactgctc tgatgcttgt acacattatt cccgatctgt tgagtgtcaa gacgcgcgaa   360
ttattcctga agaacaaggc tgaagagctt gacagggaga tgggacttat tcttactcaa   420
gaagagactg gaaggcatgt tagaatgttg actcatgaaa ttaggagcac acttgacagg   480
catactattt taaagactac tcttgtggag ttggggagga ctttgggctt ggaggagtgt   540
gcattatgga tgccttcaag aagtggtctg aatctgcaac tttcccatac tttaacctac   600
cacgtgcaag ttgggtctac agtgcaaaca aacaatccta ttgtcaatga agttttcaac   660
agtcctcgag ctatgcggat accaccaacc tgtccactgg ccaggatcag acctcttgtg   720
ggaagatatg tgccgcctga agttgttgct gttcgggtgc cacttctaaa tttgtccaat   780
tttcaaatca acgattggcc cgatatgtca gcaaaaagct atgcaatcat ggttctcatc   840
ctccctactg atagtgttag aaaatggcga gaccatgagt tggaacttgt tgatgtggtt   900
gcagatcagg tagcagttgc cctttcacat gctgctattt tggaggagtc tatgcgagcc   960
cgtgatcaac tcttggagca gaatgtcgct ttagatttag ctcggcaaga ggcagagatg  1020
gcaattcatg cccgcaacga ttttcttgcc gtcatgaatc atgaaatgag gacgccaatg  1080
catgcaatta tagcattgtc atcccttctc ttggagactg aactgactcc agagcagagg  1140

```
gttatgatag agacagtgtt gaagagtagt aatgttttgg cgacactcat taatgatgtt    1200
ctagatcttt ctcgacttga agatggtagc ctcgaattag aaaagggaaa attcaacctt    1260
catggtgttt tgggagagat cgttgaactg ataaaaccaa tagcatctgt gaaaaagtta    1320
cctatcacct taattctgtc tcctgatctg cctactcatg ccattggtga tgaaaagcga    1380
cttacacaaa ctcttttgaa tgttgtgggt aatgctgtca aattcactaa ggagggctat    1440
gtttctataa gagtatcggt tgcaaaacca gaatctttac aggattggcg acctccagag    1500
ttttatccag catctagtga tggccatttc tacatacgag tccaggttaa ggactctgga    1560
tgtggcattc ccccacaaga aattccgcat ctctttacca gtttgccca gtctcggagt     1620 ggaccagctc gacctagcag tggtgcaggt cttgggcttg ccatttgtaa agatttgta     1680 aacctcatgg gaggccacat atggattgag agtgagggtc ctgacaaagg aagcacagct    1740
acatttataa tcaaacttga gatttgtggc aatccagatc catccgatca tcaagctgca    1800
aacagaagcc aagcatacag tggaagtggt ggcctcgcta gatttaaacc cttcatcaaa    1860
gatgaagacg acactggttt ttctactaga cgcaatcaaa gaagtttcta a             1911
```

<210> SEQ ID NO 4
<211> LENGTH: 636
<212> TYPE: PRT
<213> ORGANISM: Glycine max

<400> SEQUENCE: 4

```
Met Met Glu Ser Cys Asp Cys Ile Asp Thr Gln Tyr Pro Pro Asp Glu
  1               5                  10                  15

Leu Leu Val Lys Tyr Gln Tyr Ile Ser Asp Val Leu Ile Ala Leu Ala
             20                  25                  30

Tyr Phe Ser Ile Pro Val Glu Leu Ile Tyr Phe Val Gln Lys Ser Ala
         35                  40                  45

Phe Phe Pro Tyr Arg Trp Val Leu Met Gln Phe Gly Ala Phe Ile Val
     50                  55                  60

Leu Cys Gly Ala Thr His Phe Ile Asn Leu Trp Thr Phe Ser Pro His
 65                  70                  75                  80

Ser Lys Ala Val Ala Val Met Thr Ile Ala Lys Val Ser Cys Ala
             85                  90                  95

Ile Val Ser Cys Ala Thr Ala Leu Met Leu Val His Ile Ile Pro Asp
            100                 105                 110

Leu Leu Ser Val Lys Thr Arg Glu Leu Phe Leu Lys Asn Lys Ala Glu
        115                 120                 125

Glu Leu Asp Arg Glu Met Gly Leu Ile Leu Thr Gln Glu Glu Thr Gly
    130                 135                 140

Arg His Val Arg Met Leu Thr His Glu Ile Arg Ser Thr Leu Asp Arg
145                 150                 155                 160

His Thr Ile Leu Lys Thr Thr Leu Val Glu Leu Gly Arg Thr Leu Gly
                165                 170                 175

Leu Glu Glu Cys Ala Leu Trp Met Pro Ser Arg Ser Gly Leu Asn Leu
            180                 185                 190

Gln Leu Ser His Thr Leu Thr Tyr His Val Gln Val Gly Ser Thr Val
        195                 200                 205

Gln Thr Asn Asn Pro Ile Val Asn Glu Val Phe Asn Ser Pro Arg Ala
    210                 215                 220

Met Arg Ile Pro Pro Thr Cys Pro Leu Ala Arg Ile Arg Pro Leu Val
225                 230                 235                 240
```

-continued

```
Gly Arg Tyr Val Pro Glu Val Ala Val Arg Val Pro Leu Leu
            245                 250                 255

Asn Leu Ser Asn Phe Gln Ile Asn Asp Trp Pro Asp Met Ser Ala Lys
        260                 265                 270

Ser Tyr Ala Ile Met Val Leu Ile Leu Pro Thr Asp Ser Val Arg Lys
    275                 280                 285

Trp Arg Asp His Glu Leu Glu Leu Val Asp Val Ala Asp Gln Val
290                 295                 300

Ala Ile Ala Leu Ser His Ala Ala Ile Leu Glu Glu Ser Met Arg Ala
305                 310                 315                 320

Arg Asp Gln Leu Leu Glu Gln Asn Val Ala Leu Asp Leu Ala Arg Arg
                325                 330                 335

Glu Ala Glu Met Ala Ile His Ala Arg Asn Asp Phe Leu Ala Val Met
            340                 345                 350

Asn His Glu Met Arg Thr Pro Met His Ala Ile Ile Ala Leu Ser Ser
        355                 360                 365

Leu Leu Leu Glu Thr Glu Leu Thr Pro Glu Gln Arg Val Met Ile Glu
    370                 375                 380

Thr Val Leu Lys Ser Ser Asn Val Leu Ala Thr Leu Ile Asn Asp Val
385                 390                 395                 400

Leu Asp Leu Ser Arg Leu Glu Asp Gly Ser Leu Glu Leu Glu Lys Gly
                405                 410                 415

Lys Phe Asn Leu His Gly Val Leu Gly Glu Ile Val Glu Leu Ile Lys
            420                 425                 430

Pro Ile Ala Ser Val Lys Lys Leu Pro Ile Thr Leu Ile Leu Ser Pro
        435                 440                 445

Asp Leu Pro Thr His Ala Ile Gly Asp Glu Lys Arg Leu Thr Gln Thr
    450                 455                 460

Leu Leu Asn Val Val Gly Asn Ala Val Lys Phe Thr Lys Glu Gly Tyr
465                 470                 475                 480

Val Ser Ile Arg Val Ser Val Ala Lys Pro Glu Ser Leu Gln Asp Trp
                485                 490                 495

Arg Pro Pro Glu Phe Tyr Pro Ala Ser Ser Asp Gly His Phe Tyr Ile
            500                 505                 510

Arg Val Gln Val Lys Asp Ser Gly Cys Gly Ile Pro Pro Gln Glu Ile
        515                 520                 525

Pro His Leu Phe Thr Lys Phe Ala Gln Ser Arg Ser Gly Pro Ala Arg
    530                 535                 540

Pro Ser Gly Ala Gly Leu Gly Leu Ala Ile Cys Lys Arg Phe Val
545                 550                 555                 560

Asn Leu Met Gly His Ile Trp Ile Glu Ser Gly Pro Asp Lys
                565                 570                 575

Gly Ser Thr Ala Thr Phe Ile Ile Lys Leu Glu Ile Cys Gly Asn Pro
            580                 585                 590

Asp Pro Ser Asp His Gln Ala Ala Asn Arg Ser Gln Ala Tyr Ser Gly
        595                 600                 605

Ser Gly Gly Leu Ala Arg Phe Lys Pro Phe Ile Lys Asp Glu Asp
    610                 615                 620

Thr Gly Phe Ser Thr Arg Arg Asn Gln Arg Ser Phe
625                 630                 635

<210> SEQ ID NO 5
<211> LENGTH: 1911
```

<212> TYPE: DNA
<213> ORGANISM: Glycine max

<400> SEQUENCE: 5

```
atgatggaat cctgtgattg tatagacaca cagtatcctc cagatgaact tctcgtaaag      60
tatcagtata tctcggatgt gctaattgct cttgcctatt tttctattcc cgtggagctc     120
atctattttg ttcagaagtc tgctttcttt ccatatagat gggtgcttat gcagtttggt     180
gcttttattg ttctctatgg agcaactcat tcataaacc tgtggacatt ctccccacac      240
tctaaggctg ttgctgttgt catgacgatt gccaaagtgt cgtgtgctat tgtgtcatgt     300
gcgactgctc tgatgcttgt acacattatt cccgatctgt tgagtgtcaa gacgcgcgaa     360
ttattcctga agaacaaggc tgaagagctt gacaggagga tgggacttat tcttactcaa     420
gaagagactg gaaggcatgt tagaatgttg actcatgaaa ttaggagcac acttgacagg     480
catactattt taaagactac tcttgtggag ttggggagga ctttgggctt ggaggagtgt     540
gcattatgga tgccttcaag aagtggtctg aatctgcaac tttcccatac tttaacctac     600
cacgtgcaag ttgggtctac agtgcaaaca acaatccta ttgtcaatga agttttcaac      660
agtcctcgag ctatgcggat accaccaacc tgtccactgg ccaggatcag acctcttgtg     720
ggaagatatg tgccgcctga agttgttgct gttcgggtgc cacttctaaa tttgtccaat     780
tttcaaatca cgattggcc cgatatgtca gcaaaaagct atgcaatcat ggttctcatc      840
ctccctactg atagtgttag aaaatggcga gaccatgagt tggaacttgt tgatgtggtt     900
gcagatcagg tagcagttgc cctttcacat gctgctattt tggaggagtc tatgcgagcc     960
cgtgatcaac tcttggagca gaatgtcgct ttagatttag ctcggcaaga ggcagagatg    1020
gcaattcatg cccgcaacga ttttcttgcc gtcatgaatc atgaaatgag gacgccaatg    1080
catgcaatta tagcattgtc atcccttctc ttggagactg aactgactcc agagcagagg    1140
gttatgatag agacagtgtt gaagagtagt aatgttttgg cgacactcat taatgatgtt    1200
ctagatcttt ctcgacttga agatggtagc ctcgaattag aaaagggaaa attcaaacctt   1260
catggtgttt gggagagat cgttgaactg ataaaaccaa tagcatctgt gaaaagtta     1320
cctatcacct taattctgtc tcctgatctg cctactcatg ccattggtga tgaaaagcga    1380
cttacacaaa ctcttttgaa tgttgtgggg aatgctgtca aattcactaa ggagggctat    1440
gtttctataa gagtatcggt tgcaaaacca gaatctttac aggattggcg acctccagag    1500
ttttatccag catctagtga tggccatttc tacatacgag tccaggttaa ggactctgga    1560
tgtggcattc ccccacaaga aattccgcat ctctttacca gtttgccca gtctcggagt     1620
ggaccagctc gacctagcag tggtgcaggt cttgggcttg ccatttgtaa agatttgta     1680
aacctcatgg gaggccacat atggattgag agtgagggtc ctgacaaagg aagcacagct    1740
acatttataa tcaaacttga gatttgtggc aatccagatc catccgatca tcaagctgca    1800
aacagaagcc aagcatacag tggaagtggt ggcctcgcta gatttaaacc cttcatcaaa    1860
gatgaagacg acactggttt ttctactaga cgcaatcaaa gaagtttcta a             1911
```

<210> SEQ ID NO 6
<211> LENGTH: 636
<212> TYPE: PRT
<213> ORGANISM: Glycine max

<400> SEQUENCE: 6

```
Met Met Glu Ser Cys Asp Cys Ile Asp Thr Gln Tyr Pro Pro Asp Glu
  1               5                  10                  15
```

```
Leu Leu Val Lys Tyr Gln Tyr Ile Ser Asp Val Leu Ile Ala Leu Ala
             20                  25                  30

Tyr Phe Ser Ile Pro Val Glu Leu Ile Tyr Phe Val Gln Lys Ser Ala
         35                  40                  45

Phe Phe Pro Tyr Arg Trp Val Leu Met Gln Phe Gly Ala Phe Ile Val
     50                  55                  60

Leu Tyr Gly Ala Thr His Phe Ile Asn Leu Trp Thr Phe Ser Pro His
 65                  70                  75                  80

Ser Lys Ala Val Ala Val Val Met Thr Ile Ala Lys Val Ser Cys Ala
                 85                  90                  95

Ile Val Ser Cys Ala Thr Ala Leu Met Leu Val His Ile Ile Pro Asp
             100                 105                 110

Leu Leu Ser Val Lys Thr Arg Glu Leu Phe Leu Lys Asn Lys Ala Glu
         115                 120                 125

Glu Leu Asp Arg Glu Met Gly Leu Ile Leu Thr Gln Glu Glu Thr Gly
     130                 135                 140

Arg His Val Arg Met Leu Thr His Glu Ile Arg Ser Thr Leu Asp Arg
145                 150                 155                 160

His Thr Ile Leu Lys Thr Thr Leu Val Glu Leu Gly Arg Thr Leu Gly
                 165                 170                 175

Leu Glu Glu Cys Ala Leu Trp Met Pro Ser Arg Ser Gly Leu Asn Leu
             180                 185                 190

Gln Leu Ser His Thr Leu Thr Tyr His Val Gln Val Gly Ser Thr Val
         195                 200                 205

Gln Thr Asn Asn Pro Ile Val Asn Glu Val Phe Asn Ser Pro Arg Ala
     210                 215                 220

Met Arg Ile Pro Pro Thr Cys Pro Leu Ala Arg Ile Arg Pro Leu Val
225                 230                 235                 240

Gly Arg Tyr Val Pro Pro Glu Val Val Ala Val Arg Val Pro Leu Leu
                 245                 250                 255

Asn Leu Ser Asn Phe Gln Ile Asn Asp Trp Pro Asp Met Ser Ala Lys
             260                 265                 270

Ser Tyr Ala Ile Met Val Leu Ile Leu Pro Thr Asp Ser Val Arg Lys
         275                 280                 285

Trp Arg Asp His Glu Leu Glu Leu Val Asp Val Ala Asp Gln Val
     290                 295                 300

Ala Ile Ala Leu Ser His Ala Ala Ile Leu Glu Glu Ser Met Arg Ala
305                 310                 315                 320

Arg Asp Gln Leu Leu Glu Gln Asn Val Ala Leu Asp Leu Ala Arg Arg
                 325                 330                 335

Glu Ala Glu Met Ala Ile His Ala Arg Asn Asp Phe Leu Ala Val Met
             340                 345                 350

Asn His Glu Met Arg Thr Pro Met His Ala Ile Ile Ala Leu Ser Ser
         355                 360                 365

Leu Leu Leu Glu Thr Glu Leu Thr Pro Glu Gln Arg Val Met Ile Glu
     370                 375                 380

Thr Val Leu Lys Ser Ser Asn Val Leu Ala Thr Leu Ile Asn Asp Val
385                 390                 395                 400

Leu Asp Leu Ser Arg Leu Glu Asp Gly Ser Leu Glu Leu Glu Lys Gly
                 405                 410                 415

Lys Phe Asn Leu His Gly Val Leu Gly Glu Ile Val Glu Leu Ile Lys
             420                 425                 430
```

```
Pro Ile Ala Ser Val Lys Lys Leu Pro Ile Thr Leu Ile Leu Ser Pro
        435                 440                 445

Asp Leu Pro Thr His Ala Ile Gly Asp Glu Lys Arg Leu Thr Gln Thr
    450                 455                 460

Leu Leu Asn Val Val Gly Asn Ala Val Lys Phe Thr Lys Glu Gly Tyr
465                 470                 475                 480

Val Ser Ile Arg Val Ser Val Ala Lys Pro Glu Ser Leu Gln Asp Trp
                485                 490                 495

Arg Pro Pro Glu Phe Tyr Pro Ala Ser Ser Asp Gly His Phe Tyr Ile
            500                 505                 510

Arg Val Gln Val Lys Asp Ser Gly Cys Gly Ile Pro Pro Gln Glu Ile
        515                 520                 525

Pro His Leu Phe Thr Lys Phe Ala Gln Ser Arg Ser Gly Pro Ala Arg
    530                 535                 540

Pro Ser Ser Gly Ala Gly Leu Gly Leu Ala Ile Cys Lys Arg Phe Val
545                 550                 555                 560

Asn Leu Met Gly Gly His Ile Trp Ile Glu Ser Glu Gly Pro Asp Lys
                565                 570                 575

Gly Ser Thr Ala Thr Phe Ile Ile Lys Leu Glu Ile Cys Gly Asn Pro
            580                 585                 590

Asp Pro Ser Asp His Gln Ala Ala Asn Arg Ser Gln Ala Tyr Ser Gly
        595                 600                 605

Ser Gly Gly Leu Ala Arg Phe Lys Pro Phe Ile Lys Asp Glu Asp Asp
    610                 615                 620

Thr Gly Phe Ser Thr Arg Arg Asn Gln Arg Ser Phe
625                 630                 635

<210> SEQ ID NO 7
<211> LENGTH: 1908
<212> TYPE: DNA
<213> ORGANISM: Glycine max

<400> SEQUENCE: 7
atggaagtct gcaattgtat tgaaccgcaa tggccagcgg atgaattgtt aatgaaatac      60
caatacatct ccgatttctt cattgcgatt gcgtattttt cgattcctct tgagttgatt     120
tactttgtga agaaatcagc cgtgtttccg tatagatggg tacttgttca gtttggtgct     180
tttatcgttc tttgtggagc aactcatctt attaacttat ggactttcac tacgcattcg     240
agaaccgtgg cgcttgtgat gactaccgcg aagtgttaa ccgctgttgt ctcgtgtgct      300
actgcgttga tgcttgttca tattattcct gatcttttga gtgttaagac tcgggagctt     360
ttcttgaaaa ataaagctgc tgagctcgac agggagatgg gacttattct tactcaagaa     420
gagactggaa ggcatgttag aatgttgact catgaaatta ggagcacact tgacaggcat     480
actattttaa agactactct tgtggagttg gggaggactt tgggcttgga ggagtgtgca     540
ttatggatgc cttcaagaag tggtctgaat ctgcaacttt cccatacttt aacctaccac     600
gtgcaagttg gtctacagt gcaaacaaac aatcctattg tcaatgaagt tttcaacagt      660
cctcgagcta tgcggatacc accaacctgt ccactggcca ggatcagacc tcttgtggga     720
agatatgtgc cgcctgaagt tgttgctgtt cgggtgccac ttctaaattt gtccaatttt     780
caaatcaacg attgggccga tatgtcagca aaaagctatg caatcatggt tctcatcctc     840
cctactgata gtgttagaaa atggcgagac catgagttgg aacttgttga tgtggttgca     900
gatcaggtag cagttgccct ttcacatgct gctattttgg aggagtctat gcgagcccgt     960
```

-continued

```
gatcaactct tggagcagaa tgtcgcttta gatttagctc ggcaagaggc agagatggca    1020
attcatgccc gcaacgattt tcttgccgtc atgaatcatg aaatgaggac gccaatgcat    1080
gcaattatag cattgtcatc ccttctcttg gagactgaac tgactccaga gcagagggtt    1140
atgatagaga cagtgttgaa gagtagtaat gttttggcga cactcattaa tgatgttcta    1200
gatctttctc gacttgaaga tggtagcctc gaattagaaa agggaaaatt caaccttcat    1260
ggtgttttgg gagagatcgt tgaactgata aaaccaatag catctgtgaa aaagttacct    1320
atcaccttaa ttctgtctcc tgatctgcct actcatgcca ttggtgatga aaagcgactt    1380
acacaaactc ttttgaatgt tgtgggtaat gctgtcaaat tcactaagga gggctatgtt    1440
tctataagag tatcggttgc aaaaccagaa tctttacagg attggcgacc tccagagttt    1500
tatccagcat ctagtgatgg ccatttctac atacgagtcc aggttaagga ctctggatgt    1560
ggcattcccc cacaagaaat tccgcatctc tttaccaagt tgcccagtc tcggagtgga    1620
ccagctcgac ctagcagtgg tgcaggtctt gggcttgcca tttgtaaaag atttgtaaac    1680
ctcatgggag gccacatatg gattgagagt gagggtcctg acaaaggaag cacagctaca    1740
tttataatca aacttgagat tgtggcaat ccagatccat ccgatcatca agctgcaaac    1800
agaagccaag catacagtgg aagtggtggc ctcgctagat ttaaaccctt catcaaagat    1860
gaagacgaca ctggttttc tactagacgc aatcaaagaa gtttctaa                 1908
```

<210> SEQ ID NO 8
<211> LENGTH: 635
<212> TYPE: PRT
<213> ORGANISM: Glycine max

<400> SEQUENCE: 8

```
Met Glu Val Cys Asn Cys Ile Glu Pro Gln Trp Pro Ala Asp Glu Leu
  1               5                  10                  15

Leu Met Lys Tyr Gln Tyr Ile Ser Asp Phe Phe Ile Ala Ile Ala Tyr
             20                  25                  30

Phe Ser Ile Pro Leu Glu Leu Ile Tyr Phe Val Lys Lys Ser Ala Val
         35                  40                  45

Phe Pro Tyr Arg Trp Val Leu Val Gln Phe Gly Ala Phe Ile Val Leu
     50                  55                  60

Tyr Gly Ala Thr His Leu Ile Asn Leu Trp Thr Phe Thr Thr His Ser
 65                  70                  75                  80

Arg Thr Val Ala Leu Val Met Thr Thr Ala Lys Val Leu Thr Ala Val
                 85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Leu Thr Gln Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Gly Leu
                165                 170                 175

Glu Glu Cys Ala Leu Trp Met Pro Ser Arg Ser Gly Leu Asn Leu Gln
            180                 185                 190

Leu Ser His Thr Leu Thr Tyr His Val Gln Val Gly Ser Thr Val Gln
        195                 200                 205
```

-continued

```
Thr Asn Asn Pro Ile Val Asn Glu Val Phe Asn Ser Pro Arg Ala Met
    210                 215                 220
Arg Ile Pro Pro Thr Cys Pro Leu Ala Arg Ile Arg Pro Leu Val Gly
225                 230                 235                 240
Arg Tyr Val Pro Glu Val Val Ala Val Arg Val Pro Leu Leu Asn
        245                 250                 255
Leu Ser Asn Phe Gln Ile Asn Asp Trp Pro Asp Met Ser Ala Lys Ser
            260                 265                 270
Tyr Ala Ile Met Val Leu Ile Leu Pro Thr Asp Ser Val Arg Lys Trp
                275                 280             285
Arg Asp His Glu Leu Glu Leu Val Asp Val Val Ala Asp Gln Val Ala
290                 295                 300
Val Ala Leu Ser His Ala Ala Ile Leu Glu Glu Ser Met Arg Ala Arg
305                 310                 315                 320
Asp Gln Leu Leu Glu Gln Asn Val Ala Leu Asp Leu Ala Arg Gln Glu
                    325                 330                 335
Ala Glu Met Ala Ile His Ala Arg Asn Asp Phe Leu Ala Val Met Asn
                340                 345                 350
His Glu Met Arg Thr Pro Met His Ala Ile Ile Ala Leu Ser Ser Leu
            355                 360                 365
Leu Leu Glu Thr Glu Leu Thr Pro Glu Gln Arg Val Met Ile Glu Thr
370                 375                 380
Val Leu Lys Ser Ser Asn Val Leu Ala Thr Leu Ile Asn Asp Val Leu
385                 390                 395                 400
Asp Leu Ser Arg Leu Glu Asp Gly Ser Leu Glu Leu Glu Lys Gly Lys
                    405                 410                 415
Phe Asn Leu His Gly Val Leu Gly Glu Ile Val Glu Leu Ile Lys Pro
                420                 425                 430
Ile Ala Ser Val Lys Lys Leu Pro Ile Thr Leu Ile Leu Ser Pro Asp
            435                 440                 445
Leu Pro Thr His Ala Ile Gly Asp Glu Lys Arg Leu Thr Gln Thr Leu
450                 455                 460
Leu Asn Val Val Gly Asn Ala Val Lys Phe Thr Lys Glu Gly Tyr Val
465                 470                 475                 480
Ser Ile Arg Val Ser Val Ala Lys Pro Glu Ser Leu Gln Asp Trp Arg
                485                 490                 495
Pro Pro Glu Phe Tyr Pro Ala Ser Ser Asp Gly His Phe Tyr Ile Arg
            500                 505                 510
Val Gln Val Lys Asp Ser Gly Cys Gly Ile Pro Pro Gln Glu Ile Pro
        515                 520                 525
His Leu Phe Thr Lys Phe Ala Gln Ser Arg Ser Gly Pro Ala Arg Pro
    530                 535                 540
Ser Ser Gly Ala Gly Leu Gly Leu Ala Ile Cys Lys Arg Phe Val Asn
545                 550                 555                 560
Leu Met Gly Gly His Ile Trp Ile Glu Ser Glu Gly Pro Asp Lys Gly
                565                 570                 575
Ser Thr Ala Thr Phe Ile Ile Lys Leu Glu Ile Cys Gly Asn Pro Asp
                580                 585                 590
Pro Ser Asp His Gln Ala Ala Asn Arg Ser Gln Ala Tyr Ser Gly Ser
            595                 600                 605
Gly Gly Leu Ala Arg Phe Lys Pro Phe Ile Lys Asp Glu Asp Thr
        610                 615                 620
Gly Phe Ser Thr Arg Arg Asn Gln Arg Ser Phe
```

```
<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: a fully
      synthesized primer sequence

<400> SEQUENCE: 9
ctattcccgt ggagctc                                                    17

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: a fully
      synthesized primer sequence

<400> SEQUENCE: 10
aagagctcga cagggagatg gg                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: a fully
      synthesized primer sequence

<400> SEQUENCE: 11
ctttgggctt ggaggagtgt gc                                              22

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: a fully
      synthesized primer sequence

<400> SEQUENCE: 12
gttgctgttc gggtgccac                                                  19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: a fully
      synthesized primer sequence

<400> SEQUENCE: 13
gggtaacgga ttgtctctc                                                  19
```

US 7,105,654 B1

ETHYLENE RECEPTOR GENE FROM *GLYCINE MAX* AND ITS USE

CROSS REFERENCE TO RELATED APPLICATIONS

Figure 1:
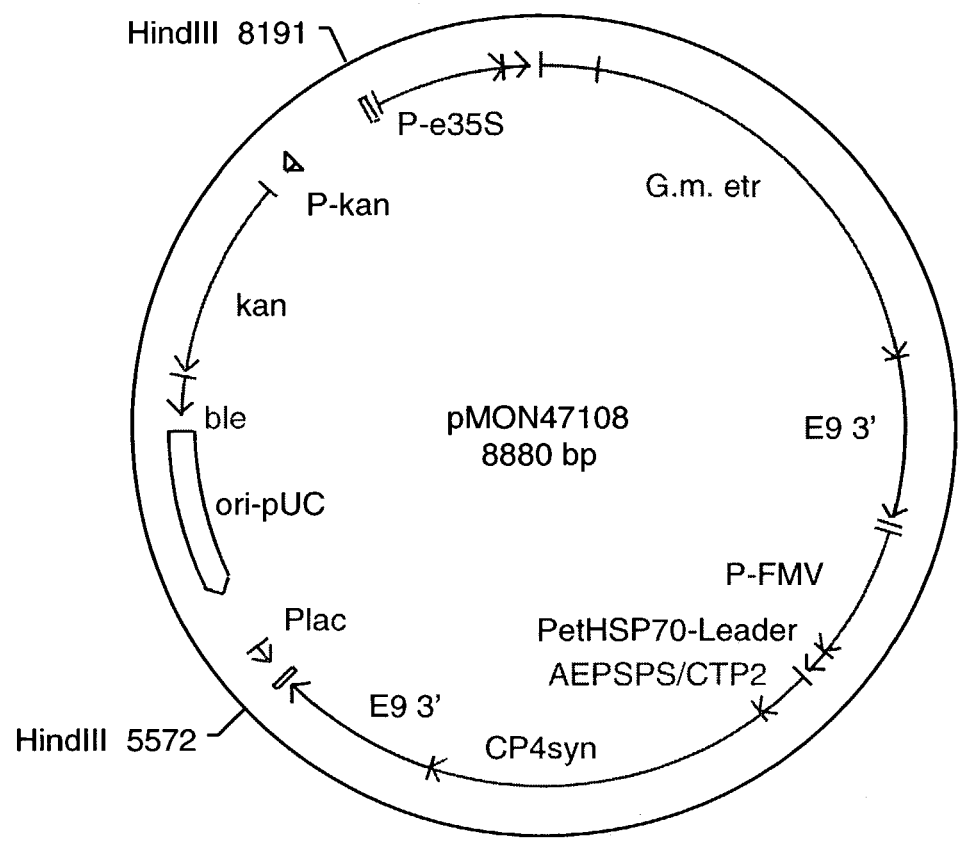

This application claims benefit under 35USC § 119(e) of U.S. provisional application Ser. No. 60/345,960 filed Jan. 2, 2002, which is herein incorporated by reference.

TECHNICAL FIELD OF THE INVENTION

The present invention relates to an isolated nucleic acid from soybean (*Glycine max*) encoding an ethylene receptor protein and a modified form thereof that is useful in improving agriculturally important traits of plants, such as yield. Specifically, the present invention relates to the isolated nucleic acid from soybean (*Glycine max*) encoding the ethylene receptor protein and a modified form thereof that can be transformed into plants for reducing ethylene-induced abscission of reproductive organs so that yield can be enhanced. The present invention also relates to plants such as soybean plants containing exogenous ethylene receptor proteins or modified exogenous ethylene receptor proteins. The present invention also relates to methods for preventing ethylene-induced abscission in plants for yield enhancement.

BACKGROUND OF THE INVENTION

Significant changes in ethylene synthesis and perception attend many of the developmental transitions experienced within a typical plant life cycle. Such ethylene-dependent processes as shoot elongation, organ abscission, fruit ripening and tissue senescence have long been presumed to be dependent upon the synthesis or activation of ethylene receptors (Trewavas, Physiol. Plant 55: 60–72, 1982). The ability to manipulate ethylene perception was advanced by the identification of ethylene receptors by genetics, positional cloning, and manipulation in transgenic plants (Bleeker et al., Science 241, 1086–1089, 1988; Wilkinson et al., Nature Biotechnology 15, 444–447, 1997; Hua and Meyerowitz, Cell 94, 261–71, 1998).

The characterization of ethylene receptors is leading to refinement of how the processes identified above may be manipulated with precision. The isolation of multiple ethylene receptor candidates and signal transduction components from different plant tissues at disparate stages of development provides a unique opportunity to assess how ethylene promotes and integrates the complex responses of plants to developmental and environmental stimuli. The identification of the roles of specific domains and their modification, the roles of specific receptors in specific tissues, and the ability to replace natural promoters with heterologous promoters all contribute to this refinement.

Several ethylene response genes have been identified in different plants. Among those identified, ETR1 (ethylene response 1) gene has been studied extensively and several ETR1 homologs have been identified and characterized (Sato-Nara et al., Plant Physiol. 119: 321–329, 1999; Lashbrook et al., Plant J. 15 (2): 243–252, 1998; Zhou et al., Plant Mol. Biol. 30: 1331–1338, 1996; Payton et al., Plant Mol. Biol. 31: 1227–1231, 1996). Available data indicate that expression of the ETR1 gene appears to be stage- and tissue-specific and to be regulated during fruit ripening, flower senescence and abscission. The ETR1 gene is expressed in vegetative and reproductive tissues (Zhou et al., Plant Mol. Biol. 30: 1331–1338, 1996) and during fruit development (Sato-Nara et al., Plant Physiol. 119: 321–329, 1999) and it appears to play important roles in plant development and senescence in relation to ethylene perception. In *Arabidopsis*, as many as five ETR1-like genes have been identified (Lashbrook et al., Plant Journal 15, 243–252, 1998; Theologis, Current Biology 8, 875–878, 1998; Chang et al., Science 262: 539–544, 1993; Hua et al., Science 269: 1712–1714, 1995; Hua et al., Plant Cell 10: 1321–1332, 1998) and they vary significantly in their protein domains. One lacks the carboxy-terminal domain known as the receiver domain while another lacks a critical histidine in the histidine kinase domain though it retains functionality as an ethylene receptor. These variations, particularly the latter, imply that functional differences do exist.

Ethylene insensitivity of plants has been studied by analysis of mutant forms of ETR genes in the homologous species, e.g. ETR1-1 in *Arabidopsis* (Bleeker et al, Sci. 241: 1086, 1988) and the never ripe mutant in tomato (Lanahan et al., Plant Cell, 6: 521–530, 1994). The ethylene receptor interacts not only with itself in dimerization but must interact with downstream components of the ethylene signal transduction pathway. Specific members of the ethylene receptor pathway may have evolved to interact with specific members of the family of genes comprising the second step in the signal transduction pathway. Because of this protein—protein interaction, use of an ethylene receptor, in its mutated form, of the homologous species and of the same target cell in which ethylene insensitivity is desired is expected to be more efficacious.

Use of an ETR1 gene in its modified form to manipulate the ethylene response in plants may have a great impact on crop yield. Thus, by providing modifications to an ETR1 nucleic acid sequence by substituting, inserting, and/or deleting one or more nucleotides so as to substitute, insert, and/or delete one or more amino acid residues in the protein encoded by the ETR1 nucleic acid, ethylene perception in a plant may be regulated when such a nucleic acid sequence is introduced and expressed in a plant cell. The expression of such a modified ETR1 protein may result in, for example, but not limited to, the retention of more soybean pods and cotton bolls during their development for maturity. To this end, yield will be increased.

In one embodiment an ETR1 nucleic acid, chimeric, mutant thereof, or a portion thereof is placed under the control of an abscission zone (AZ) enhanced promoter, in either a sense or an anti-sense orientation. The promoter could show greater transcriptional enhancement in one AZ or another, for example the pedicel AZ. The expression of this transcript in the AZ could lead to greater retention of reproductive organs, and greater yield.

SUMMARY OF THE INVENTION

Therefore, the present invention, in one aspect, relates to an isolated nucleic acid molecule from soybean (*Glycine max*) encoding ethylene receptor proteins. The isolated nucleic acid molecule comprises a full-length ETR1 nucleic acid sequence from a cDNA that comprises 1911 nucleotides encoding a polypeptide with 636 amino acid residues having SEQ ID NO: 4. The sequence of the ETR1 nucleic acid comprises SEQ ID NO: 3.

The present invention, in another aspect, provides an isolated nucleic acid from *Glycine max* comprising a nucleotide sequence, wherein the nucleotide sequence is defined as follows: (1) the nucleotide sequence is identical to a sequence comprising SEQ ID NO: 3; (2) the nucleotide sequence hybridizes under stringent conditions to the complement of a second isolated nucleic acid, wherein the nucleotide sequence of the second isolated nucleic acid comprising SEQ ID NO: 3; or (3) the nucleotide sequence is complementary to (1) or (2).

The present invention, in still another aspect, provides an isolated nucleic acid from *Glycine max* comprising a nucleotide sequence, wherein the nucleotide sequence is defined as follows: (1) the nucleotide sequence encodes a polypeptide having an amino acid sequence that is identical to a sequence comprising SEQ ID NO: 4; (2) the nucleotide sequence hybridizes under stringent conditions to the complement of a second isolated nucleic acid, wherein the nucleotide sequence of the second isolated nucleic acid encodes a polypeptide having an amino acid sequence comprising SEQ ID NO: 4; or (3) the nucleotide sequence is complementary to (1) or (2).

The present invention, in yet another aspect, also relates to a recombinant DNA construct for transformation into plants for yield enhancement. The construct comprises an abscission zone specific promoter, an ETR1 structural nucleic acid sequence and a regulatory element. The ETR1 structural nucleic acid sequence may be a modified sequence in any form using available technologies. In one example of the present invention, the structural ETR1 nucleic acid sequence is a mutated form of the ETR1 nucleic acid sequence of the present invention that encodes a polypeptide on which Cysteine 66 is converted to Tyrosine. The mutated polypeptide sequence comprises SEQ ID NO: 6. In another example, the ETR1 structural nucleic acid sequence may be a chimeric one that comprises a portion of the ETR1 nucleotide of the present invention from *Glycine max* and a portion from any other available ETR1 nucleic acid sequence from any species. In a preferred embodiment, the chimeric gene may comprise a 5' N-terminal portion from *Arabidopsis thaliana* and a 3' C-terminal portion of the ETR1 nucleic acid sequence of the present invention, which encodes a chimeric polypeptide having SEQ ID NO: 8. The recombinant DNA construct causes reduction of the indigenous ETR protein level upon its transformation into crop plants where the introduced, modified ETR1 structural nucleic acid sequence or a fragment thereof binds to a native ETR protein and makes the ETR protein complex non-functional. With the reduction of the native ETR protein level in the crop plants the crop plants are insensitive to ethylene. Thus, the ethylene-induced abscission of the reproductive organs of the crop plants such as flowers, pods and bolls may be reduced and yield enhanced.

The present invention, in yet another aspect, also relates to transgenic crop plants that demonstrate insensitivity to ethylene. These transgenic crop plants contain exogenous ETR1 nucleic acid sequences or fragments thereof. In one example of the present invention, the exogenous ETR1 nucleic acid is a mutated form of the ETR1 nucleic acid sequence of the present invention that encodes a polypeptide on which Cysteine 66 is converted to Tyrosine. The mutated polypeptide sequence comprises SEQ ID NO: 6. In another example of the present invention, the exogenous ETR1 nucleic acid sequence is chimeric that comprises a portion of the ETR1 nucleic acid sequence of the present invention and a portion of an available ETR1 nucleic acid sequence from any species. In a preferred embodiment, the chimeric gene may be a portion of the ETR1 nucleic acid sequence of the present invention and a portion from *Arabidopsis*, which encode a chimeric polypeptide having SEQ ID NO: 8.

The present invention, in yet still another aspect, also provides a method of producing transgenic crop plants with reduced ETR protein levels in comparison to that of the wild type crop plants. Through reduction of the ETR protein levels in the transgenic crop plants the transgenic plants will demonstrate insensitivity to ethylene. In a preferred embodiment, the levels of the functional ETR proteins in the transgenic crop plants may be reduced by binding indigenous ETR1 mRNAs with exogenous ETR1 nucleic acid sequences that comprise mutated ETR1 nucleic acid sequences encoding polypeptides having SEQ ID NO: 6. In another preferred embodiment, the levels of the functional ETR proteins in the transgenic crop plants may be reduced by binding indigenous ETR1 mRNAs with exogenous ETR1 nucleic acid sequences that comprise chimeric ETR1 nucleic acid sequences encoding chimeric polypeptides having SEQ ID NO: 8.

Other and further objectives and aims of the invention will be made clear or covered from the following description and claims when read in light of the accompanying drawings.

BRIEF DESCRIPTION OF THE DRAWINGS AND SEQUENCES

FIG. 1 shows a map of pMON47108. HindIII fragment (clockwise from 8191 to 5572) was excised and introduced by particle bombardment to *Glycine max*. Abbreviations: G.m. ETR, Coding region of the mutated *Glycine max* ethylene receptor gene described herein.

Figure 2:
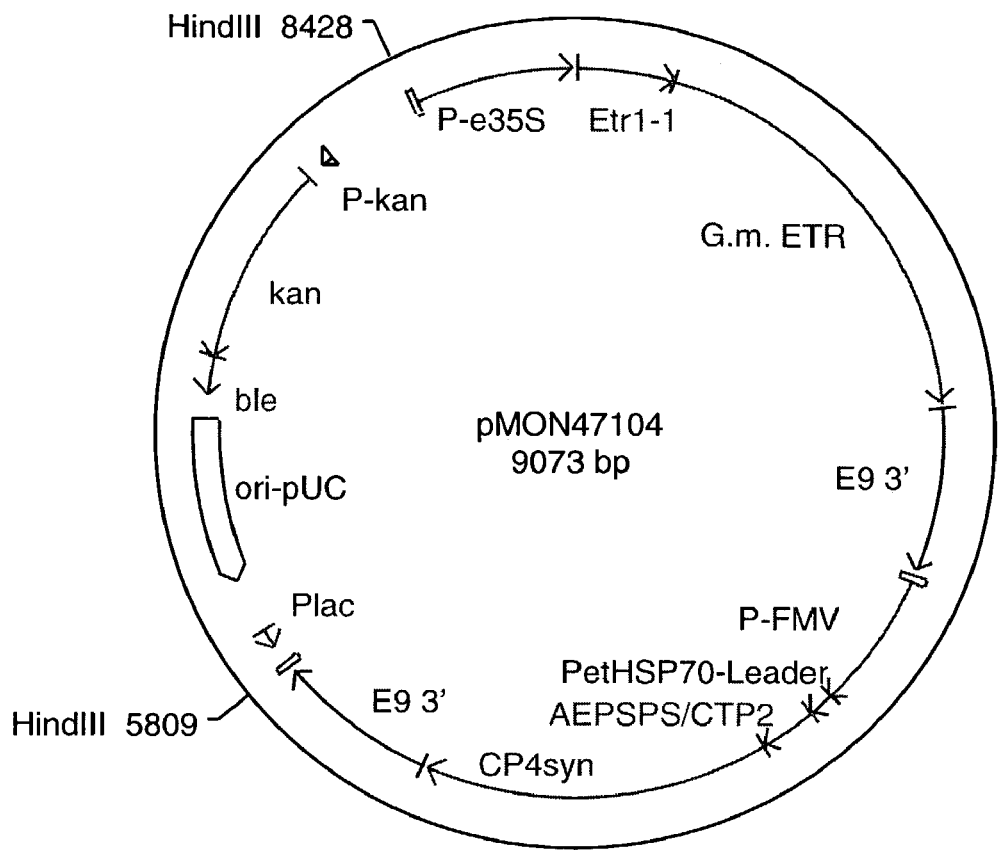

FIG. 2 shows a map of pMON47104. HindIII fragment (clockwise from 8428 to 5809) was excised and introduced by particle bombardment to *Glycine max*. Abbreviations: ETR1-1, ethylene binding domain of the *Arabidopsis thaliana* ETR1-1 gene; G.m. ETR, C-terminal domain of the *Glycine max* ethylene receptor gene described herein.

Figure 3:
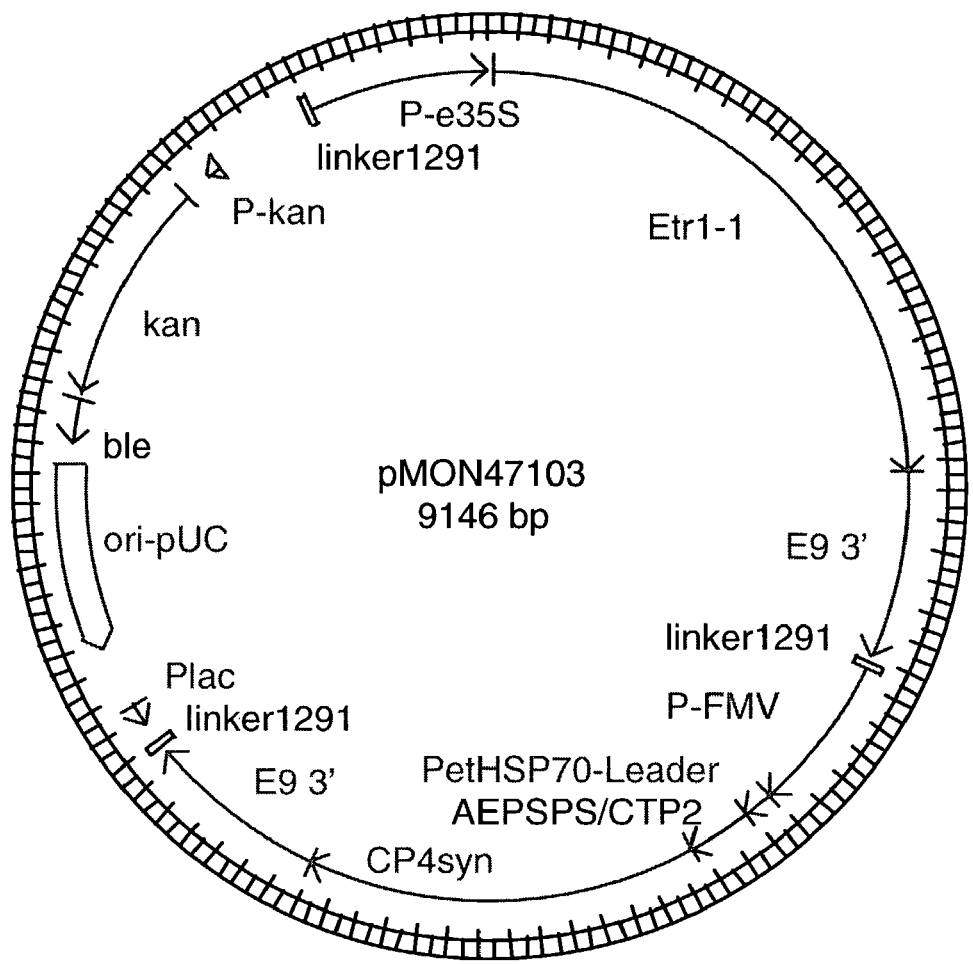

FIG. 3 shows a map of pMON 47103 with the *Arabidopsis thaliana* ETR1-1 gene.

Figure 4:
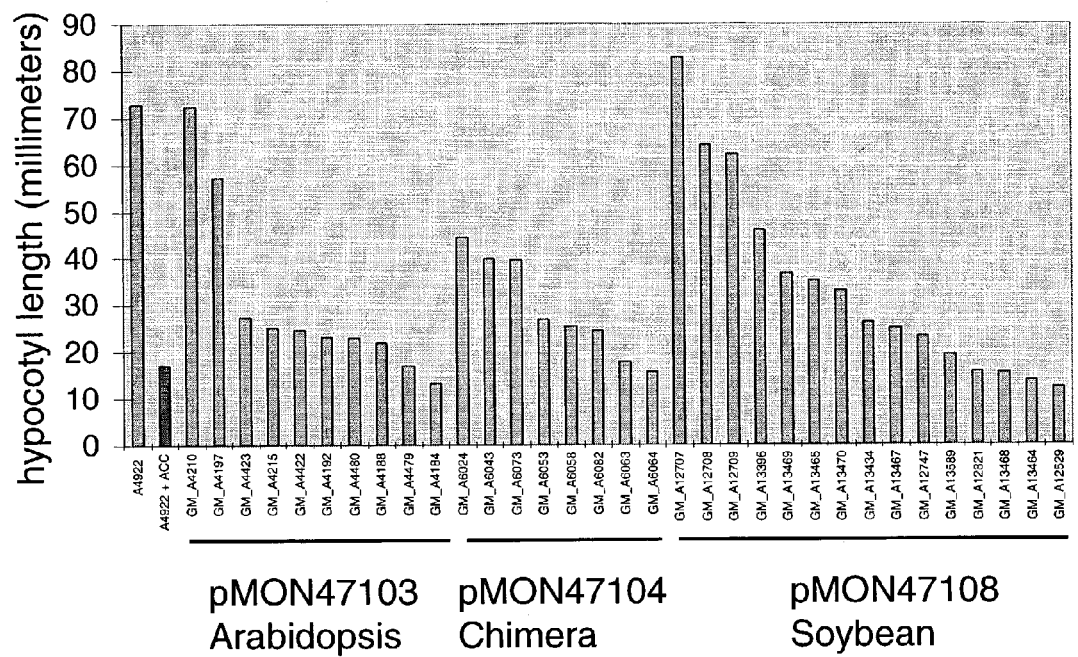

FIG. 4. R1 seeds from pMON47103, pMON47104, and pMON47108 were screened by an ACC insensitivity assay. On average, ten R1 seeds from each event were screened by growing them in media containing 1-amino cyclopropane-1-carboxylate (ACC) except for the bar furthest left that shows a wild type soybean cultivar A4922 grown without ACC. Hypocotyl length was measured after six days and the average value presented.

Figure 5:
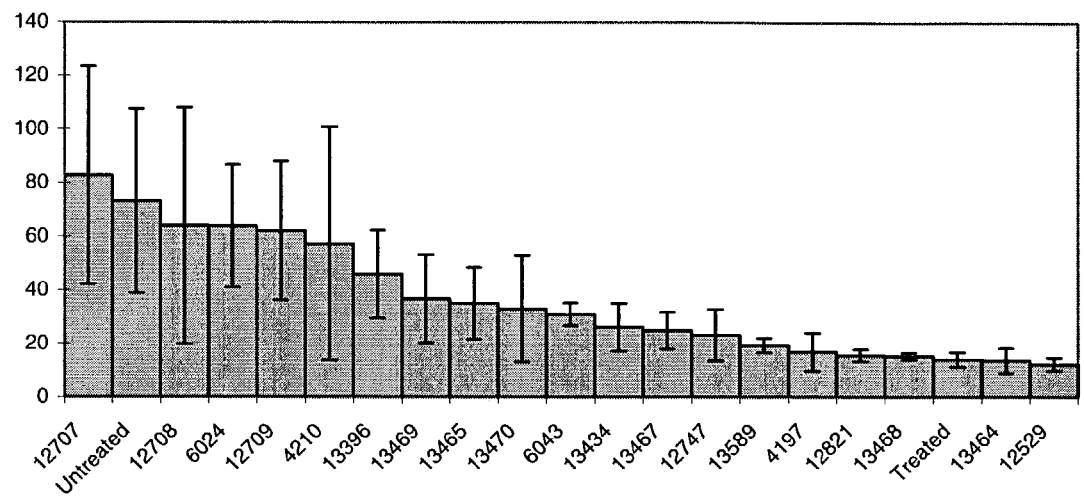

FIG. 5. The average hypocotyl length (in millimeter) response of transgenic and control soybean plants in response to ethylene in presence of 500 uM ACC. Hypocotyl length represents ethylene insensitivity efficacy. The transgenic plants contain pMON 47108 with a mutated soybean ETR1 structural gene. The events that exhibited the longest hypocotyls were those selected for the abscission experiment shown in FIG. 6 below. "Untreated": control plant not treated with ACC; "treated": control plant treated with ACC.

Figure 6:
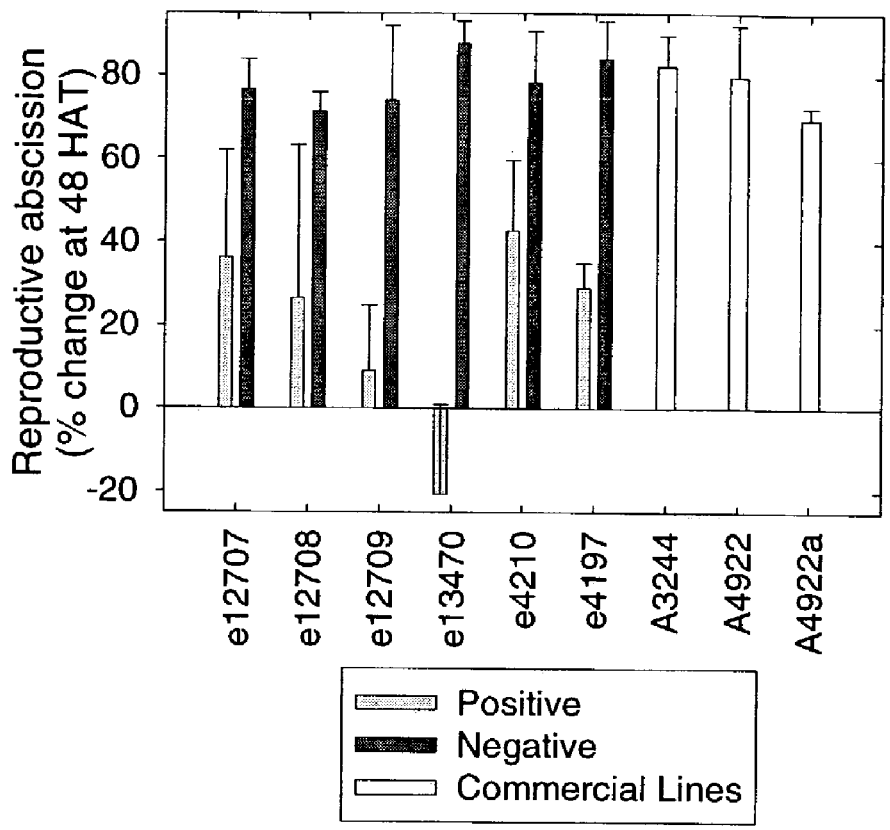

FIG. 6 shows a reproductive structure abscission rate in soybean plants following ⅝ pint per acre ethephon treatment. Data shown is 48 hours after treatment. Data represent mean and standard error of 5 plants. Gray bars, transgenic plants containing pMON 47108; black bars, nontransgenic plants of the same species as the transgenic plants; open bars, nontransgenic plants from commercial lines. The abscission rate was calculated as: (number of flowers at time of ethephon treatment—number of flowers 48 hours after treatment)/number of flowers at time of ethephon treatment.

SEQ ID NO: 1: First primer sequence designed to create the desired mutation on the wild type ethylene receptor nucleic acid sequence.

SEQ ID NO: 2: Second primer sequence designed to create the desired mutation on the wild type ethylene receptor nucleic acid sequence.

SEQ ID NO: 3: The nucleotide sequence of the wild type *Glycine max* ethylene receptor.

SEQ ID NO: 4: Predicted amino acid sequence of the wild type *Glycine max* ethylene receptor.

SEQ ID NO: 5: Nucleotide sequence of the modified *Glycine max* ethylene receptor.

SEQ ID NO: 6: Predicted amino acid sequence of the modified *Glycine max* ethylene receptor. The mutated ethylene receptor has Cysteine 66 converted to Tyrosine.

SEQ ID NO: 7: Nucleotide sequence of the chimerical *Arabidopsis thaliana* ETR1-1*Glycine max* ethylene receptor gene. The SacI restriction site is the site where ligation of the composite nucleotide sequences occurred.

SEQ ID NO: 8: Predicted amino acid sequence of the chimerical *Arabidopsis thaliana* ETR1-1/*Glycine max* ethylene receptor. The portion from *Glycine max* is mutated wherein Tyrosine 66 is converted from Cysteine of the wild type.

SEQ ID NO:9: A sequencing primer used to clone the ETR gene from soybean *Glycine max*.

SEQ ID NO:10: A sequencing primer used to clone the ETR gene from soybean *Glycine max*.

SEQ ID NO:11: A sequencing primer used to clone the ETR gene from soybean *Glycine max*.

SEQ ID NO:12: A sequencing primer used to clone the ETR gene from soybean *Glycine max*.

SEQ ID NO:13: A sequencing primer used to clone the ETR gene from soybean *Glycine max*.

DETAILED DESCRIPTION OF THE PREFERRED EMBODIMENTS

Many agronomic traits can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. For example, these could also include, without limitation, efficiency of germination (including germination in stressed conditions), growth rate (including growth rate in stressed conditions), ear number, seed number per ear, seed size, composition of seed (starch, oil, protein), characteristics of seed fill. "Yield" can be measured in may ways, these might include test weight, seed weight, seed number per plant, seed weight, seed number per unit area (i.e. seeds, or weight of seeds, per acre), bushels per acre, tonnes per acre, tons per acre, kilo per hectare. In an embodiment, a plant of the present invention might exhibit an enhanced trait that is a component of yield.

"Reproductive organ" includes any numbers of organs of any type related to reproduction, including creation and propagation of meiotic products including but not limited to pollen, stamen, pistil, ovum, as well as pods, flowers, and seeds. Reproductive organ is also inclusive of asexually produced products that can result in another plant (even a clone). Reproductive organ is specifically inclusive of flower, fruit, vegetable, grain, pod, flower, and seed, but is not limited to these.

As used herein, a "coding sequence", "structural nucleotide sequence" or "structural gene" is a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence may include, but may not be limited to, genomic DNA, cDNA, and recombinant nucleotide sequences.

As used herein, a "C-terminal region" refers to the region of a peptide, polypeptide, or protein chain from the middle thereof to the end that carries the amino acid having a free carboxyl group. A "N-terminal region" refers to the region of a peptide, polypeptide, or protein chain from the amino acid having a free amino group to the middle of the chain.

As used herein, an ethylene response nucleic acid, or "ETR nucleic acid", refers to nucleic acid encoding all or part of an ethylene receptor protein, or "ETR protein". An ethylene response 1 nucleic acid, or "ETR1 nucleic acid", refers to a nucleic acid encoding all or part of a specific ethylene receptor 1 protein, or "ETR1 protein". The ETR nucleic acids may include any ETR nucleic acids from any source. An exemplary ETR nucleic acid is the ETR1 nucleic acid as described above, that has been studied extensively. Transformation with an ETR nucleic acid or modified ETR nucleic acid can result in suppression of the endogenous ETR alleles that in turn modifies the ethylene response. Further, an ETR1 nucleic acids can be modified for use in the present invention which when it is used to transform plant tissue results in varying degrees of ethylene insensitivity in the tissue expressing such a modified ETR1 nucleic acid.

As used herein, the term "modified ETR nucleic acid" refers to an ETR nucleic acid containing substitution, insertion or deletion of one or more nucleotides of an original ETR nucleic acid. The original ETR nucleic acids include naturally occurring ETR nucleic acids as well as other modified ETR nucleic acids.

As used herein, "expression" refers to the transcription and stable accumulation of mRNA derived from the nucleic acid of the invention. Expression may also refer to translation of mRNA into a polypeptide. Also as used herein, "overexpression" refers to the production of a gene product in transgenic organisms that exceeds levels of production in normal or non-transformed organisms.

As used herein, a "genotype" refers to the genetic constitution, latent or expressed, of a plant, the sum total of all genes present in an individual. As used herein, a "phenotype" of a plant is any of one or more characteristics of a plant (e.g. male sterility, yield, quality improvements, etc.), as contrasted with the genotype. A change in genotype or phenotype may be transient or permanent.

As used herein, a "homolog" of a nucleotide sequence refers to an isolated nucleic acid sequence that is substantially the same as the ETR1 nucleic acid sequence of the present invention or its complementary nucleotide sequence. A "homolog" of the ETR1 nucleic acid sequence is a polynucleotide sequence from a plant species that encodes a polypeptide that is functionally similar to ETR1 and that preferably has substantial amino acid sequence identity or similarity to ETR1 from soybean.

As used herein, "hybridization" refers to the ability of a strand of nucleic acid to join with a complementary strand via base pairing. Hybridization occurs when complementary sequences in the two nucleic acid strands bind to one another.

As used herein, "identical" nucleotide or protein sequences are determined by using programs such as a BLAST program (Altschul et al., Nucleic Acids Res. 25:3389–3402; 1997) using the default parameters (Expectation value (E): blank; Alignment view options: pairwise; Filter query sequence: no; Cost to open a gap: 0; Cost to extend a gap: 0; X dropoff value for gapped alignment: 0; Show GI's in deflines: no; Penalty for a nucleotide mismatch: −3; Reward for a nucleotide match: 1; Threshold for extending hits: 0; Perform gapped alignment: yes; Query Genetic code to use: standard; DB Genetic code: standard; Believe the query defline: no; Matrix: BLOSUM62; Word size: 0; Effective length of the database: 0; Query strand Use: both).

As used herein, an "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

As used herein, the term "polypeptide" or "protein", refers to a polymer composed of amino acids connected by peptide bonds. The term "polypeptide" or "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties*, 2nd ed. (Creighton, Freeman and Company, N.Y., 1993). Many detailed reviews are available on this subject, such as, for example, those provided by Wold (In: *Post-translational Covalent Modification of Proteins*, Johnson, Academic Press, N.Y., pp. 1–12, 1983), Seifter et al. (*Meth. Enzymol.* 182: 626, 1990) and Rattan et al. (*Ann. N.Y. Acad. Sci.* 663: 48–62, 1992). Modifications can occur anywhere in a polypeptide, including the peptide backbone, the amino acid side chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine containing and the methionine-less amino terminal variants of the protein of the invention. Thus, as used herein, the term "protein" or "polypeptide" includes any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids.

As used herein, the term "isolated polypeptide" refers primarily to a polypeptide produced by expression of an isolated nucleic acid molecule of the present invention or by chemically synthesizing process. Alternatively, this term may refer to a polypeptide that has been sufficiently separated from other polypeptides or proteins with which it would naturally be associated, so as to exist in substantially pure form. Also as used herein, a "functionally equivalent fragment" of the isolated polypeptide refers to a polypeptide that lacks at least one residue from an end of a native full length ETR1 polypeptide. Such a fragment retains ETR1 activity when expressed in a transgenic plant or possesses a characteristic functional domain or an immunological determinant characteristic of a native ETR1 polypeptide. Immunologically active fragments typically have a minimum size of 7 or 17 or more amino acids. Preferably, ETR1 fragments are at least 10 amino acids in length.

As used herein, the term "native" refers to a naturally occurring ("wild type") nucleic acid or polypeptide.

As used herein, a "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. The percentage of sequence identity may be determined by using programs such as a BLAST program (Altschul et al., Nucleic Acids Res. 25:3389–3402, 1997) using the default parameters.

As used herein, a "promoter" refers to a DNA sequence capable of controlling the expression of a coding sequence or functional RNA. In general, a coding sequence is located 3' to a promoter sequence. The promoter sequence consists of proximal and more distal upstream elements, the later elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters. Promoters that cause conditional expression of a structural nucleotide sequence under the influence of changing environmental conditions or developmental conditions are commonly referred to as "inducible promoter".

As noted above, the present invention provides a recombinant DNA construct or expression vector that facilitates the expression of the ETR1 nucleic acid sequence discussed herein in plants. As used herein, the term "recombinant DNA construct" refer to assemblies of DNA fragments through genetic engineering operatively linked in a functional manner that direct the expression of the ETR1 nucleic acid sequence discussed herein, as well as any additional sequence(s) or gene(s) of interest in the plants.

As used herein, "regeneration" refers to the process of growing a plant from a plant cell or tissue (e.g., plant protoplast or explant).

As used herein, "sequence homology" refers to nucleic acid or polypeptide sequence that has certain percentage of nucleotide or amino acid similarity, as used in the present invention, to a native ETR1 nucleic acid or polypeptide sequence or ETR1 nucleic acid or polypeptide sequence. Ordinarily, if a ETR1 nucleic acid or polypeptide sequence encompassed by the present invention has at least about 70% nucleotide or amino acid similarity to a native ETR1 nucleic acid or polypeptide sequence or to a ETR1 nucleic acid, preferably at least 80%, more preferably at least about 90%, and most preferably at least about 95% similarity, such sequence homology is considered to be substantial homology.

As used herein, the term "sequence identity" refers to amino acid or nucleic acid sequences that when compared using the local homology algorithm of Smith and Waterman in the BestFit program (Wisconsin Package Version 10.0, Genetics Computer Group (GCG), Madison, Wis., 1981) are exactly alike.

As used herein, the term "sequence similarity" refers to amino acid sequences that when compared using the local homology algorithm of Smith and Waterman in the BestFit program (Wisconsin Package Version 10.0, Genetics Computer Group (GCG), Madison, Wis., 1981) match when conservative amino acid substitutions are considered.

As used herein, a "stringent condition" is functionally defined with regard to hybridization of a nucleic-acid probe to a target nucleic acid (i.e., to a particular nucleic acid sequence of interest) by the specific hybridization procedure discussed in Sambrook et al. (Molecular Cloning: A Laboratory Manual, Cold Spring Harbor Laboratory Press, Cold Spring Hobart, 1989, at 9.52–9.55). Regarding the amplification of a target nucleic acid sequence (e.g., by PCR) using a particular amplification primer pair, "stringent conditions" are conditions that permit the primer pair to hybridize substantially only to the target nucleic acid sequence to which a primer having the corresponding wild-type sequence (or its complement) would bind so as to produce a unique amplification product. For hybridization of a probe or primer to a polynucleotide of another plant species in order to identify homologs, preferred hybridization and washing conditions are as discussed in Sambrook et al (supra, at 9.47–9.57, wherein "high stringent conditions" include hybridization at 65° C. in a hybridization solution that includes 6×SSC and washing for 1 hour at 65° C. in a wash solution that include 0.5×SSC, 0.5% SDS. "Moderate stringency" conditions are similar except that the temperature for the hybridization and washing steps are performed at a lower temperature at which the probe is specific for a target sequence, preferably at least 42° C., more preferably at least 50° C., more preferably at least 55° C., and more preferably at least 60° C.

As used herein, a "tissue sample" is any sample that comprises more than one cell. In a preferred aspect, a tissue sample comprises cells that share a common characteristic (e.g., derived from a leaf, a root, or a pollen, or from an abscission layer, etc).

As used herein, a "3"untranslated region" or "3' untranslated nucleic acid sequence" or "3' transcriptional termination signal" refers to a piece of transcribed but untranslated nucleic acid sequence at the 3' end that functions in a plant cell to cause transcriptional termination and/or the addition of polyadenylate nucleotides to the 3' end of said RNA sequence. Typically, a DNA sequence located from four to a few hundred base pairs downstream of the polyadenylation site serves to terminate transcription. The region is required for efficient polyadenylation of transcribed messenger RNA (mRNA). RNA polymerase transcribes a coding DNA sequence through a site where polyadenylation occurs.

As used herein, "transformation" refers to the transfer of a nucleic acid fragment into the genome of a host organism such as a host plant, resulting in genetically stable inheritance. Host plants containing the transformed nucleic acid fragments are referred to as "transgenic plants".

Unless otherwise defined, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. Standard recombinant DNA and molecular cloning techniques used herein are well known in the art and are described in detail in Sambrook et al. (Molecular Cloning: A Laboratory Manual, Cold Spring Harbor Laboratory Press, Cold Spring Harbor, 1989).

The ethylene Response 1 (ETR1) Gene and Protein

Under one of the objects, the present invention is directed to an isolated ethylene response 1 (ETR1) nucleic acid that encodes an ethylene receptor 1 protein. As disclosed in the present invention, the ETR1 nucleic acid disclosed herein is isolated from a soybean plant, i.e., *Glycine max*, and is a full length ETR1 cDNA sequence comprising 1911 nucleotides. Its ETR1 protein comprises 636 amino acid residues.

In a preferred embodiment, an isolated nucleic acid molecule of the present invention may comprise a nucleotide sequence or complement thereof, wherein the nucleotide sequence encodes a polypeptide having an amino acid sequence identical to SEQ ID NO: 4.

The isolated nucleic acid of the present invention may also comprise a nucleotide sequence or complement thereof, wherein the nucleotide sequence encodes a polypeptide having an amino acid sequence set forth in SEQ ID NO: 4 with conservative amino acid substitutions.

In a preferred embodiment, an isolated nucleic acid molecule of the present invention may comprise a nucleotide sequence or complement thereof, wherein the nucleotide sequence has at least 90% sequence identity to SEQ ID NO: 3.

In a further preferred embodiment, an isolated nucleic acid molecule of the present invention may comprise a nucleotide sequence or complement thereof, wherein the nucleotide sequence has at least 95% sequence identity to SEQ ID NO: 3.

In a more preferred embodiment, an isolated nucleic acid molecule of the present invention may comprise a nucleotide sequence or complement thereof, wherein the nucleotide sequence has at least 98% sequence identity to SEQ ID NO: 3.

In a most preferred embodiment, an isolated nucleic acid molecule of the present invention may comprise a nucleotide sequence or complement thereof, wherein the nucleotide sequence is identical to SEQ ID NO: 3.

Under one object, the present invention relates generally to plant molecular biology and plant genetic engineering. More specifically, the present invention relates to and isolated nucleic acid having SEQ ID NO: 3 encoding an ETR1 protein having SEQ ID NO: 4 that is useful in improving agronomic, horticultural and quality traits of plants, such as yield. In addition, proteins and fragments thereof so encoded and antibodies capable of specifically binding to the proteins are encompassed by the present invention. The disclosed nucleic acid molecules, proteins, fragments of proteins, and antibodies, for example, for gene identification and analysis, preparation of constructs, transformation of plant cells, production of transgenic plants characterized by increased yield are also encompassed by the present invention.

Under another object, the present invention is directed to a method for manipulating ETR1 gene expression in transgenic plants to reduce ethylene-induced abscission of reproductive structures. For this purpose, the ETR1 nucleic acid used in the present invention is not necessarily the ETR1 nucleic acid disclosed herein. Any ETR1 nucleic acids available in the art may be manipulated using the methods disclosed herein for utilization in the present invention and these ETR1 nucleic acids may include the sequences from *Arabidopsis* (U.S. Pat. No. 5,689,055), *Pisum sativum* (AJ005829), *Vigna radiata* (AF098272), *Carita papaya* (AF311942) and *Passiflora edulis* (AB015497). The species provided herein are just a few examples of ETR1 sequences that can be readily available for use in the present invention and thus should not be interpreted in any way to limit the scope of the present invention. The ETR1 nucleotide sequence used in the present invention can be a full length or a fragment of any of the ETR1 nucleotide sequences from any species. Those skilled in the art will be able to identify other ETR1 sequences from different species and alterations/modifications that can be made to the ETR1 sequences and method disclosed herein while not departing from the scope of the present invention.

Preparation of a cDNA Library

Complementary DNA (cDNA) libraries from a soybean plant may be prepared according to standard techniques known to those skilled in the art, for instance, in Sambrook et al., Molecular Cloning—A Laboratory Manual, Cold Spring Harbor Laboratory, Cold Spring Harbor, N.Y., (1989). Using conventional methodologies, cDNA libraries can be constructed from the mRNA of a given tissue sample or an organ using poly dT primers and reverse transcriptase (Efstratiadis et al., Cell 7:279–288, 1976; Higuchi et al., Proc. Natl. Acad. Sci. (U.S.A.) 73:3146–3150, 1976; Maniatis et al., Cell 8:163, 1976; Land et al., Nucleic Acids Res. 9:2251–2266, 1981; Okayama et al., Mol. Cell. Biol. 2:161–170, 1982; Gubler et al., Gene 25: 263, 1983). Several methods may be employed to obtain full-length cDNA constructs. For example, terminal transferase can be used to add homopolymeric tails of dC residues to the free 3' hydroxyl groups (Land, et al., Nucleic Acids Res. 9:2251–2266, 1981). This tail can then be hybridized by a poly dG oligo that can act as a primer for the synthesis of full-length second strand cDNA. A simplified method has been developed by using synthetic primer-adapters that have both homopolymeric tails for priming the synthesis of the first and second strands and restriction sites for cloning into plasmids (Coleclough et al., Gene 34:305–314, 1985) and bacteriophage vectors (Krawinkel et al., Nucleic Acids Res. 14:1913, 1986; and Han et al., Nucleic Acids Res. 15: 6304, 1987).

A method to enrich preparations of mRNA for a sequence of interest is to fractionate by size. One such method is to fractionate by electrophoresis through an agarose gel (Pennica et al., Nature 301:214–221, 1983). Another such method employs sucrose gradient centrifugation in the presence of an agent, such as methylmercuric hydroxide, that denatures secondary structure in RNA (Schweinfest, et al., Proc. Natl. Acad. Sci. (U.S.A.) 79:4997–5000, 1982).

A frequently adopted method is to construct equalized or normalized cDNA libraries (Ko, Nucleic Acids Res. 18:5705–5711, 1990; Patanjali et al., Proc. Natl. Acad. Sci. (U.S.A.) 88:1943–1947, 1991). Typically, the cDNA population is normalized by subtractive hybridization (Schmid et al., J. Neurochem. 48:307–312, 1987; Fargnoli et al., Anal. Biochem. 187:364–373, 1990; Travis et al., Proc. Natl. Acad. Sci (U.S.A.) 85:1696–1700, 1988; Kato, Eur. J. Neurosci. 2: 704, 1990; and Schweinfest al., Genet. Anal. Tech. Appl. 7: 64, 1990). Subtraction represents another method for reducing the population of certain sequences in the cDNA library (Swaroop et al., Nucleic Acids Res. 19:1954, 1991).

In one of the preferred embodiments, preparation of appropriately enriched cDNA libraries from tissue of interest such as a tissue sample from the abscission layer of a soybean plant may be described as below. Soybean plants that have gone special drought treatment may be used to build the cDNA library. The soybean plants may be grown in a greenhouse and, when they reach a pod-initiating stage, they may be treated with no irrigation. The plants that have been treated with non-irrigation for 3–6 days may be used for collection of the abscission zone specific tissues. The cDNA library may be constructed using techniques known to those skilled in the art. Briefly, mRNA from the tissue sample may be isolated and cDNA prepared. Short chains of oligo d-T nucleotides may be hybridized with the poly-A tails of the mRNA and serve as a primer for the enzyme, reverses transcriptase, which synthesizes a complementary DNA (cDNA) strand. The cDNA may be enriched for the desired sequences using subtraction hybridization procedures following Davis et al. (Proc. Natl. Acad. Sci. USA 81: 2194–2198, 1984). The quality of the cDNA library may be determined by examining the cDNA insert size, and also by sequence analysis of a random selection of an appropriate number of clones from the library.

Amplification of the Nucleic Acid from the cDNA Library

As described herein, any particular nucleic acid molecule from the cDNA library, such as the annotation of the cDNA library from the soybean plant, may be amplified through use of many available methods. The most preferred method of achieving such a goal may employ the polymerase chain reaction ("PCR") using primer pairs that are capable of hybridizing to the proximal sequences that define the annotation of the cDNA library in its double-stranded form.

Other known nucleic acid amplification procedures, such as oligonucleotide ligation assay (OLA), allele-specific oligomers, branched DNA technology, transcription-based amplification systems, or isothermal amplification methods may also be used to amplify and analyze the nucleic acid molecule, such as the annotation of the cDNA library from the soybean plant.

Sequencing of the Nucleic Acid from the cDNA Library

The nucleic acid molecule, such as the annotation of the cDNA library from the soybean plant may be sequenced after its amplification through use of many available methods. The most preferred method of achieving such a goal may employ the PCR, as described above, using primer pairs that are capable of hybridizing to the proximal sequences that define the annotation of the cDNA library in its double-stranded form.

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., Genome Analysis: Analyzing DNA, 1, Cold Spring Harbor, N.Y., 1997).

Modification of the Nucleic Acid Sequence

Site-directed mutagenesis may be utilized to modify nucleic acid sequences, such as the sequence of the ETR1 nucleic acid, particularly as it is a technique that allows one or more of the amino acids encoded by a nucleic acid molecule to be altered (e.g. a Cysteine to be replaced by a Tyrosine). Three basic methods for site-directed mutagenesis are often employed. These are cassette mutagenesis (Wells et al., Gene 34:315–23, 1985), primer extension (Gilliam et al., Gene 12:129–137, 1980; Zoller and Smith, Methods Enzymol. 100:468–500, 1983; Dalbadie-McFarland et al., Proc. Natl. Acad. Sci. (U.S.A.) 79:6409–6413, 1982) and methods based upon PCR (Scharf et al., Science 233:1076–1078, 1986; Higuchi et al., Nucleic Acids Res. 16:7351–7367, 1988). The site-directed mutagenesis strategies have been applied to plants for both in vitro as well as in vivo site-directed mutagenesis.

In one of the preferred embodiments in the present invention, the ETR1 nucleic acid molecules may either be modified by the site-directed mutagenesis strategies or used as, for example, nucleic acid molecules that are used to target other nucleic acid molecules for modification. The ETR1 nucleic acid modified by any available methodologies as described above may be referred as the modified ETR1 nucleic acid and the protein that is encoded by the modified ETR1 nucleic acid as the modified ETR1 protein. It is understood that mutants with more than one altered nucleotides can be constructed using techniques that practitioners skilled in the art are familiar with such as isolating restriction fragments and ligating such fragments into an expression vector (see, for example, Sambrook et al., Molecular Cloning: A Laboratory Manual, Cold Spring Harbor Press, 1989).

Construction of a Chimeric Protein

The coding sequence of the ETR1 gene of the present invention can be extensively altered, for example, by fusing part of it to the coding sequence of a different gene to produce a novel hybrid gene that encodes a fusion protein or chimeric protein. A chimeric protein may be made by a conventional method available in the art, see, for example, Sambrook et al., Molecular Cloning: A Laboratory Manual, Cold Spring Harbor Press, 1989. A chimeric protein disclosed in the present invention may be made by combining any two available ETR nucleic acid sequences that encode ETR1 proteins. In one example of the present invention, the chimeric protein may be produced by fusing part of the soybean ETR1 nucleic acid sequence that encodes C-terminal portion of the soybean ETR1 protein to part of the *Arabidopsis* ETR1 nucleic acid sequence that encode the ethylene binding domain of the *Arabidopsis* ETR1 protein.

Promoter Selection and Vector Construction

Exogenous genetic material such as the mutated or chimeric ETR1 nucleic acid may be transferred into a plant cell by use of a DNA vector or construct designed for such a purpose. Design of such a vector is generally within the skill of the art (See, Plant Molecular Biology: A Laboratory Manual, Clark eds, Springer, New York, 1997).

A construct or vector may include a plant promoter to express a protein or a protein fragment of choice. A number of promoters that are active in plant cells have been described in the literature and have been used to create DNA constructs that have been expressed in plants (see, e.g., PCT patent application WO 84/02913). These promoters include the nopaline synthase (NOS) promoter (Ebert et al., Proc. Natl. Acad. Sci. (U.S.A.) 84:5745–5749, 1987), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., Plant Mol. Biol. 9:315–324, 1987) and the CAMV $^{35}$S promoter (Odell et al., Nature 313:810–812, 1985), the figwort mosaic virus 35S-promoter, the light-inducible promoter from the small subunit of ribulose-1,5-bis-phosphate carboxylase (ss-RUBISCO), the Adh promoter (Walker et al., Proc. Natl. Acad. Sci. (U.S.A.) 84:6624–6628, 1987), the sucrose synthase promoter (Yang et al., Proc. Natl. Acad. Sci. (U.S.A.) 87:4144–4148, 1990), the R gene complex promoter (Chandler et al., The Plant Cell 1:1175–1183, 1989), and the chlorophyll a/b binding protein gene promoter, etc. Promoters that are known or are found to cause transcription of DNA such as mentioned above can be used for DNA transcription in target tissues or cell types. Such promoters may be obtained from a variety of sources such as plants and plant viruses. It is preferred that the particular promoter selected should be capable of causing sufficient expression to result in the production of an effective amount to cause the desired phenotype. In addition to promoters which are known to cause transcription of DNA in plant cells, other promoters may be identified for use in the current invention by screening a plant cDNA library for nucleic acids which are selectively or preferably expressed in the target tissues or cells. For example, for the purpose of expression in source tissues of the plant, such as the leaf, seed, root or stem, it is preferred that the promoters utilized have relatively high expression in these specific tissues. Similarly, for the purpose of expression of a DNA of interest in sink tissues of the plant, such as the tuber of the potato plant, the fruit of tomato, or the seed of maize, wheat, rice, and barley, it is preferred that the promoters utilized have relatively high expression in these specific tissues. These promoters may be tissue-specific or show enhanced expression in these tissues.

For the purpose of expression of the ETR1 nucleic acid in abscission layers of plants such as in those of soybean plants, as described in the present invention, it is preferred that the promoters utilized in the present invention have relatively high expression in these specific tissues. For this purpose, one may choose from a number of promoters for genes with tissue- or cell-specific expression. One may also choose from a number of promoters for genes with enhanced expression in these tissues or cells. Examples of such promoters reported in the literature include a MADS domain transcription, factor promoter, a cellulase promoter and a polygalacturonase promoter. In one of the preferred embodiments, the promoter may be the enhanced CaMV 35S promoter (P-e35S). The preferred promoter may also be one with enhanced expression in pedicel abscission layer cells in comparison to all other cells. The pedicel abscission layer is that distal to the raceme of soybean and proximal to the pedicel supporting the flower. The promoters may also be useful if they show enhanced expression in abscission layer cells more generally, including those of the petiole, the pod dehiscence zone, and the layer distal to the funiculum and proximal to the hilum.

The vector or construct may also include a structural gene or a fragment of the structural gene thereof. The structural gene may be operatively linked downstream to a promoter as described above. The structural gene may be expressed at a high level under control of a preferred promoter in all cell tissue types or in a specific tissue of a crop plant of interest, for example, a soybean plant. In one preferred embodiment, the structural gene may be an ETR gene from any source and may be a mutated form of the ETR nucleic acid or a chimeric ETR nucleic acid including a portion of the ETR nucleic acid from one species and another portion from another species. Specifically, the structural gene may be a modified ETR1 nucleic acid sequence from any source or a chimeric ETR1 nucleic acid sequence including a portion of the ETR1 nucleic acid from one species and another portion from another species. In one of the preferred embodiments, the ETR1 nucleic acid may be from a soybean plant (*Glycine max*) in a mutated form. It may be useful that the coding region may contain a mutation at a site in the amino terminal ethylene binding domain. In another preferred embodiment, the chimeric protein may be produced by fusing part of the soybean ETR1 nucleic acid sequence that encodes a C-terminal portion of the soybean ETR1 protein to part of the *Arabidopsis* ETR1 nucleic acid sequence that encodes the ethylene binding domain of the *Arabidopsis thaliana* ETR1 protein. It may be useful that the chimeric coding region may contain the histidine kinase domain of the ETR1 nucleic acid sequence in combination with a mutated amino terminal ethylene binding domain. It would be also useful that the coding region may contain only the histidine kinase domain and completely lack the amino terminal ethylene binding domain and transmembrane regions.

The vector or construct may also include, within the coding region of interest, a nucleic acid sequence that acts, in whole or in part, to terminate transcription of that region. For example, such sequences that have been isolated include the Tr7 3' sequence and the nos 3' sequence (Ingelbrecht et al., The Plant Cell 1:671–680, 1989; Bevan et al., Nucleic Acids Res. 11:369–385, 1983) or the like.

The vector or construct may also include regulatory elements. Examples of such regulatory elements may include the Adh intron 1 (Callis et al., Genes and Develop. 1:1183–1200, 1987), the sucrose synthase intron (Vasil et al., Plant Physiol. 91:1575–1579, 1989), and the TMV omega element (Gallie et al., The Plant Cell 1:301–311, 1989). These and other regulatory elements may be included when appropriate.

The vector or construct may also include a selectable marker, a screenable marker and other elements as appropriate. Examples of these elements and markers mentioned herein are known in the art and may be readily used in the present invention.

Methods and compositions for transforming bacteria and other microorganisms are known in the art (see for example Sambrook et al., Molecular Cloning: A Laboratory Manual, Second Edition, Cold Spring Harbor Laboratory Press, Cold Spring Harbor, N.Y., 1989).

Plant Transformation

The ETR1 nucleic acid molecules of the present invention may be transferred into a plant cell and the plant cell regenerated into a whole plant. The ETR1 nucleic acid molecules may be from any source, whether naturally occurring or otherwise obtained through methodologies in the field that are readily known to those skilled in the art, that are capable of being inserted into any plant cells. The ETR1 nucleic acid molecules may be transferred into either monocotyledonous or dicotyledonous plants (Chistou, Particle Bombardment for Genetic Engineering of Plants, Biotechnology Intelligence Unit, Academic Press, San Diego, Calif., 1996).

There are many methods for transforming the ETR1 nucleic acid molecules into plant cells such as the soybean plant cells. Suitable methods are believed to include virtually any methods by which nucleic acid molecules may be introduced into the cells, such as by *Agrobacterium* infection or direct delivery of nucleic acid molecules that may include PEG-mediated transformation" electroporation and acceleration of DNA coated particles, etc. (Pottykus, Ann. Rev. Plant Physiol. Plant Mol. Biol. 42:205–225, 1991; Vasil, Plant Mol. Biol. 25: 925–937, 1994). In general, the following are four most commonly used general methods for delivering a gene into cells: (1) chemical methods (Graham and van der Eb, Virology, 54:536–539, 1973); (2) physical methods such as microinjection (Capecchi, Cell 22:479–488, 1980), electroporation (Wong and Neumann, Biochem. Biophys. Res. Commun. 107:584–587, 1982; Fromm et al., Proc. Natl. Acad. Sci. (USA) 82:5824–5828, 1985) and the gene gun (Johnston and Tang, Methods Cell Biol. 43:353–365, 1994); (3) viral vectors (Clapp, Clin. Perinatol. 20:155–168, 1993; Lu et al., J. Exp. Med. 178: 2089–2096, 1993; Eglitis and Anderson, Biotechniques 6:608–614, 1988); and (4) receptor-mediated mechanisms (Curiel et al., Hum. Gen. Ther. 3: 147–154, 1992; Wagner et al., Proc. Natl. Acad. Sci. (USA) 89: 6099–6103, 1992).

Transformation of plant protoplasts can be achieved using methods based on calcium phosphate precipitation, polyethylene glycol treatment, electroporation, and combinations of these treatments. See for example (Potrykus et al., Mol. Gen. Genet. 205:193–200, 1986; Lorz et al., Mol. Gen. Genet. 199:178, 1985; Fromm et al., Nature 319:791, 1986; Uchimiya et al., Mol. Gen. Genet. 204: 204, 1986; Callis et al., Genes and Development 1183, 1987; Marcotte et al., Nature 335:454, 1988). Application of these systems to different plant strains depends upon the ability to regenerate that particular plant strain from protoplasts. Illustrative methods for the regeneration of cereals from protoplasts are also described (Fujimura et al., Plant Tissue Culture Letters, 2:74, 1985; Toriyama et al., Theor. Appl. Genet. 205:34, 1986; Yamada et al., Plant Cell Rep. 4: 85, 1986; Abdullah et al., Biotechnology 4:1087, 1986).

In one of the preferred embodiments, the present invention may be implemented by using a particle gun as described above (Johnston and Tang, Methods Cell Biol. 43:353–365, 1994). The modified ETR1 nucleic acid molecules may be coated on particles and projected into plants tissues ballistically. In another preferred embodiments, the present invention may employ the *Agrobacterium*-mediated transformation technology to introduce the modified ETR1 nucleic acid into the soybean plant and to achieve a desired result. *Agrobacterium*-mediated transfer is a widely applicable system for introducing genes such as the modified ETR1 gene into plant cells. The use of *Agrobacterium*-mediated plant integrating vectors to introduce a nucleic acid into plant cells is well known in the art. See, for example, Fraley et al. (Biotechnology 3:629–635, 1985), Hiei et al. (U.S. Pat. No. 5,591,616), and Rogers et al. (Meth. In: Enzymol 153: 253–277, 1987). Further, the integration of the Ti-DNA is a relatively precise process resulting in few rearrangements. The region of the ETR1 nucleic acid to be transferred is defined by the border sequences and is usually inserted into the plant genome as described in Spielmann et al. (Mol. Gen. Genet. 205:34, 1986).

A transgenic plant such as a transgenic soybean plant formed using the above-mentioned transformation methods may contain a single added ETR1 gene on one chromosome. Such a transgenic plant can be referred to as being heterozygous for the added ETR1 gene. More preferred is a transgenic plant that is homozygous for the added ETR1 gene; i.e., a transgenic plant that contains two added ETR1 genes, one gene at the same locus on each chromosome of a chromosome pair. A homozygous transgenic plant can be obtained by sexually mating (selfing) an independent segregated transgenic plant that contains a single added ETR1 gene, germinating some of the seeds produced and analyzing the resulting plants produced for the ETR1 gene.

It is understood that two different transgenic plants can also be mated to produce offspring that contains two independently segregating added, exogenous ETR1 genes. Selfing of appropriate progeny can produce plants that are homozygous for both added, exogenous ETR1 genes that encode ETR1 polypeptides. Back-crossing to a parental plant and out-crossing with a non-transgenic plant are also contemplated, as is vegetative propagation.

Regeneration of the Transformed Plants

The regeneration, development, and cultivation of plants such as the soybean plants from transformants or from various transformed explants containing a foreign, exogenous gene that encodes a protein of interest are well known in the art (Weissbach and Weissbach, In: Methods for Plant Molecular Biology, Eds, Academic Press, Inc. San Diego, Calif., 1988). This regeneration and growth process may typically include the steps of selection of transformed cells containing exogenous ETR1 genes, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The regenerated plants such as the regenerated soybean plants that contain the modified ETR1 nucleic acids, either wild type or chemically synthesized, that encode for the ETR1 proteins, may be preferably self-pollinated to provide homozygous transgenic soybean plants, as discussed before. Otherwise, pollen obtained from the regenerated soybean plants may be crossed to seed-grown plants of agronomically important lines. Conversely, pollen from plants of these important lines is used to pollinate regenerated plants. A transgenic soybean plant of the present invention may be cultivated using methods well known to one skilled in the art.

There are a variety of methods for the regeneration of plants from plant tissue. The particular method of regeneration will depend on the starting plant tissue and the particular plant species to be regenerated. Monocotyledonous plants, or monocot plants, may be transformed with an ETR1 nucleic acid and then regenerated. Transformation and plant regeneration have been achieved in many monocot plants that include maize, asparagus, barley and wheat. Dicotyledonous plants, or dicot plants, may also be transformed with modified ETR1 nucleic acid and regenerated. Methods for transforming dicot plants and obtaining transgenic plants have been published, including methods for soybean, cotton, and other dicot plants.

Monocot and dicot plants to which the present invention may be applied may include those agronomic and horticultural crop plants. Examples of agronomic crop plants may include cereals such as maize, wheat, rye, barley, oats, buckwheat, sorghum and rice; non-cereals such as sunflower, canola, peas, beans, soybeans, cotton and linseed; vegetables such cauliflower, asparagus, lettuce, tobacco and mustard; and root crops such as sugarbeet, potato, sweet potato, carrot and turnip. Horticultural crops may include celery, tomato, egg plant, cucumber and squash. Fruit crops may include apple, apricot, peach, pear, plum, orange, blackberry, blueberry, strawberry, cranberry and lemon.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see, for example, Sambrook et al., Molecular Cloning: A Laboratory Manual, Cold Spring Harbor Press, 1989; Mailga et al., Methods in Plant Molecular Biology, Cold Spring. Harbor Press, 1995; Birren et al., Genome Analysis: Analyzing DNA, 1, Cold Spring Harbor, N.Y., 1997). The entirety of which is hereby incorporated by reference hereto.

The following examples further demonstrate several preferred embodiments of the present invention. Those skilled in the art will recognize numerous equivalents to the specific embodiments described herein. Such equivalents are intended to be within the scope of the present invention and claims.

EXAMPLES

Example 1

Preparation of Soybean Abscission Layer Library

A cDNA library was generated from the abscission zone of drought stressed soybean cultivar Asgrow 3244 at R3 reproductive stage. The term "R3" as used herein refers to the reproductive stage of plant development for soybean in which plants are 58 to 81 cm (23 to 32 inches) tall and have a 5 mm (3/16 inch) long pod at one of the four uppermost nodes on the main stem with a fully developed leaf. The reproductive stages of soybean development are subdivided and designated R1 (beginning bloom), R2 (full bloom), R3 (beginning pod), R4 (full pod), R5 (beginning seed), R6 (full seed), R7 (beginning maturity) and R8 (full maturity). These designations are well known to those of skill in the art (see, for example, How a Soybean Plant Develops, special report No. 53, Iowa State University of Science and Technology, Cooperative Extension Service, Ames, Iowa, 1996).

Seeds were planted in moist METRomix 350 medium at a depth of approximately 2 cm. Plants were placed in an environmental chamber set to 12 h day/12 h night cycle; 26° C. daytime temperature, 21° C. night temperature; 70% relative humidity. Daytime light levels were measured at 300 microeinsteins per square meter. Plants were irrigated with 15-16-17 Peter's Mix. At the R3 stage of development, drought was imposed by stopping irrigation. At 3, 4, 5, and 6 days, tissue was harvested. Wilting was not obvious until the fourth day. Abscission layers from reproductive organs were collected by cutting less than one millimeter proximal and distal to the layer. Immediately upon excision, samples were frozen in liquid nitrogen and transported on dry ice. The following tissues were combined for the single library: four day stress with all nodes and five day stress with all nodes.

For the cDNA library of the present invention, components of both the Superscript™ Plasmid System for cDNA synthesis and Plasmid Cloning (Gibco BRL, Life Technologies, Gaithersburg, Md.) and the SMART™ PCR cDNA Library Construction Kit (Clontech Laboratories, Inc, Palo Alto Calif.) were used. Total RNA was isolated from the node tissue. The cDNA was synthesized by first generating first strand cDNA from total RNA using the Superscript II enzyme (Gibco BRL, Life Technologies, Gaithersburg, Md.) and the SMART oligo from the SMART™ PCR cDNA Library Construction Kit. The cDNA was then PCR amplified using the appropriate primers supplied in the SMART™ PCR cDNA Library Construction Kit, resulting in amplified double stranded cDNA. Sal I adaptors from the Superscript™ Plasmid System were ligated to the cDNA, followed by digestion with the Not I enzyme. After size fractionation, the cDNA was ligated into the pSPORT 1 cloning vector. The quality of the cDNA libraries was determined by examining the cDNA insert size, and also by sequence analysis of a random selection an appropriate number of clones from the library.

Example 2

Sequencing an Annotation of Soybean Abscission Layer Library

The cDNA library was plated on LB agar containing the appropriate antibiotics for selection and incubated at 37° C. for a sufficient time to allow the growth of individual colonies. Single colonies were individually placed in each well of 96-well microtiter plates containing LB liquid including the selective antibiotics. The plates were incubated overnight at approximately 37° C. with gentle shaking to promote growth of the cultures. The plasmid DNA was isolated from each clone using a commercially available kit such as Qiaprep plasmid isolation kits, using the conditions recommended by the manufacturer (Qiagen Inc., Santa Clarita, Calif.). A variety of plasmid isolation kits are commercially available.

The template plasmid DNA clones were used for subsequent sequencing. For sequencing the cDNA library, a commercially available sequencing kit, such as the ABI PRISM dRhodamine Terminator Cycle Sequencing Ready Reaction Kit with AmpliTaq® DNA Polymerase, FS, was used under the conditions recommended by the manufacturer (PE Applied Biosystems, Foster City, Calif.). ESTs were generated by sequencing initiated from the 5' end of each cDNA clone.

Annotation of the EST sequences was accomplished by utilizing a number of different search algorithms, one example of which was the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, Trends in Biotechnology, 12: 76–80, 1994; Birren, et al., Genome Analysis, 1: 543–559, 1997). Utilization of these programs resulted in ability to assign hit identities for individual EST sequences.

Example 3

Identification and Mutation of a Soybean ETR1 Gene

Clone LIB3107-016-Q1-K1-D4 is a Monsanto cDNA clone identified by its expressed sequence tag and annotation as being an ETR gene from soybean (*Glycine max*) encoding an ethylene receptor. Five primers were designed to sequence and to confirm the insertion of the cDNA clone following the procedure as disclosed in Sambrook et al. (Molecular Cloning: A Laboratory Manual, Cold Spring Harbor Laboratory Press, Cold Spring Harbar, 1989). These primers were SEQ ID NO: 9 (5'CTATTCCCGTGGAGCTC3'), SEQ ID NO: 10 (5'AAGAGCTCGACAGGGAGATGGG3'), SEQ ID NO: 11 (5'CTTTGGGCTTGGAGGAGTGTGC3'), SEQ ID NO: 12 (5'GTTGCTGTTCGGGTGCCAC3') and SEQ ID NO: 13 (5'GGGTAACGGATTGTCTCTC3'). The nucleotide sequence of the insert contained in the cDNA clone is confirmed to be the wild type ethylene response 1 gene encoding an ETR1 polypeptide. The isolated ETR1 nucleic acid sequence comprises SEQ ID NO: 3. The predicted amino acid sequence of the wild type ethylene receptor is shown as SEQ ID NO: 4.

To create the desired mutation on the wild type ethylene receptor nucleic acid sequence, primers of the desired sequences, i.e., 5'GCTTTTATTGTTCTCTATGGAGCAACTCATTTC3' (SEQ ID NO: 1) and 5'GAAATGAGTTGCTCCATAGAGAACAATAAAAGC3' (SEQ ID NO: 2), were synthesized and used in combination with the QuikChange Site-Directed Mutagenesis Kit of Stratagene. Plasmid DNA was denatured and annealed to the primers. PfuTurbo™ Polymerase was used to extend and incorporate the mutation primers resulting in nicked circular strands. The parental DNA template was digested and remaining plasmids were transformed into *E. coli*, which repaired nicks in the plasmid and propagated the plasmid. The modified ethylene receptor nucleic acid sequence that is mutated from the wild type ethylene receptor nucleic acid sequence is shown as SEQ ID NO: 5 and the predicted amino acid sequence as SEQ ID NO: 6.

Example 4

Preparation of the Vector Constructs

One gene constructed as found in pMON47108 (see FIG. 1) contained the mutated soybean ethylene receptor (SEQ ID NO: 5, as in Example 3). Another gene constructed as found in pMON47104 (see FIG. 2) contained a chimeric gene (SEQ ID NO: 7) comprised of two portions: a 5' end (encoding 129 amino acids) derived from the *Arabidopsis thaliana* ETR1-1 gene and a 3' end (encoding 506 amino acids) derived from the soybean ethylene receptor gene of the present invention. The portion derived from the soybean ethylene receptor gene encodes entirely the histidine kinase domain of the receptor. The predicted amino acid sequence is shown as SEQ ID NO: 8.

Example 5

Plant Transformation and Regeneration

The expression cassettes were cut from the vectors to remove vector backbone. For example, for pMON47104 and pMON47108, HindIII digest separated the backbone from transformation cassette containing both a selectable marker cassette and a gene expression cassette. Vector backbone was separated from the transformation cassette by high performance liquid chromatography (HPLC). DNA was coated onto gold particles and introduced to meristem explants using the Accell gun.

Bombarded meristems were transferred to growth media and incubated until capable to form roots. Explants were transferred to rooting medium containing glyphosate and incubated until an extensive root system was developed. Plantlets were transplanted to soil and grown to maturity. Seeds were collected for further use. The transformation protocol for soybean glyphosate selection was as described in U.S. Pat. No. 5,914,451.

Example 6

Screening of Transgenic Material for Ethylene Insensitivity

Seeds were germinated in growth pouches (Mega International, Minneapolis, Minn.) containing 25 milliliters of 25 micromolar 1-aminocyclopropane-1-carboxylic acid (ACC) (Sigma Chemical Company) or in tissue culture boxes containing agar, water, and 20 micromolar ACC. Seedlings were kept in the dark for seven days. Growth of hypocotyl and root were scored in comparison to seedlings grown in water with all other conditions identical. An alternative protocol was used to measure growth in a solid matrix. Vermiculite was placed in a 4"×4" plastic pot to ½" below the rim. Twelve seeds were placed in each pot beneath the surface of the vermiculite. A solution of 500 micromolar ACC in distilled water was used to saturate the vermiculite. The pots were placed in a tray with additional solution to ensure a supply during incubation. The plants were incubated in a dark ventilated cabinet at room temperature for six days. On the sixth day, seedlings were removed from the vermiculite and rinsed. The hypocotyl length (from first lateral root to the bend of the apical hook) was measured and compared against wild type plants grown in the same environmental condition. Wild type plants grown similarly except without ACC were also used as controls.

Following growth in the dark for a period of days without ACC, control nontransformed soybean variety Asgrow A4922 reached on average a height of greater than 70 millimeters (FIG. 3, far left). In response to applied ACC, Asgrow A4922 seedlings reached, on average, a height less than 20 millimeters (FIG. 3, second from left). All R1 transgenic families were tested in the presence of ACC. All three constructs, pMON47103, pMON447104, and pMON47108 produced segregating families that on average were completely or highly insensitive to the applied ACC (FIG. 3, displayed in each group to the left). The heights of several individuals within these families exceeded the height of the controls. In contrast, some families displayed complete sensitivity to ACC (FIG. 3, displayed in each group to the right). Variability within events was expected due to segregation of the introduced transgene. Variability between events was also expected since bombarded fragments may not be integrated into the genome intact or due to effects resulting from position of integration within the genome. Homozygous lines will be derived from families displaying insensitivity to ACC. After homozygous lines are obtained and re-tested, the variability of insensitivity is in expectation to be reduced.

Example 7

Screening for Pod Retention

Seeds were planted in the field in 12-foot rows with 8 seeds per foot and 30 inches between rows. Plots were laid out in a randomized, replicated design. At reproductive stages R3, R4, R5, or maturity (see Example 1), 8 plants per row were harvested for pod mapping. Number of branches including main stem, number of nodes, and number of pods per node was recorded for each plant within a row. Pod number and distribution were scored in comparison to control plants grown within the replica. Results across replicas and locations were combined. R2 seeds derived from single R1 plants are planted in the field as described. Screening of twelve individuals from each row by enzyme-linked immunosorbent assay of the selectable marker CP4 allows determination of which rows are derived from a homozygous parent. Homozygous rows will be mapped as described. As insensitivity to ACC and ethylene is expected to reduce abscission of pods, the number of pods per node is expected to increase in lines containing an effective transgene. After harvest, seed derived from the rows analyzed for pod retention will be re-screened to confirm that insensitivity to ACC is retained.

Example 8

Screening for Increased Yield

Seeds are planted in the field in 12-foot rows with 8 seeds per foot and 30 inches between rows. Plots are laid out in a randomized, replicated design. Each row is harvested separately. Pounds of seed per plot and moisture are determined. Pounds of seeds per plot are corrected to 13% moisture and are scored in comparison to control plants grown within the replica. Results from replicates within a location and across several locations are combined.

R3 seeds derived from pooled plants from a single R2 row will be planted in the field as described. At maturity, the number of pods per node may be re-determined to confirm results obtained in the R2 generation. Similarly, the derived R4 seed may be re-screened to confirm stability of the insensitivity to ACC. As the number of pods per node is one component of yield, it is expected that yield will be increased in the lines displaying insensitivity to ACC and ethylene.

In summary, the above describes the present invention. It will be understood by those skilled in the art that, without departing from the scope and spirit of the present invention and without undue experimentation, the invention can be performed within a wide range of equivalent parameters. While the present invention has been described in connection with specific embodiments thereof, it will be understood that it is capable of further modifications. The present invention covers any uses, variations, or adaptations of the invention following the principles of the invention in general. Various permutations and combination of the elements provided in all the claims that follow are possible and fall within the scope of this invention.

All publications and patents mentioned in this specification are herein incorporated by reference as if each individual publication or patent was specially and individually stated to be incorporated by reference.

We claim:

1. An isolated nucleic acid molecule, comprising a soybean nucleotide sequence encoding an ethylene receptor protein having an amino acid sequence that is at least 95% identical over the full length of SEQ ID NO: 6, wherein the amino acid at position 66 is tyrosine.

2. The isolated nucleic acid molecule of claim 1, comprising the nucleotide sequence as set forth in SEQ ID NO: 5 or the complement thereof.

3. A recombinant DNA construct, comprising a structural nucleotide sequence encoding an ethylene receptor protein having an amino acid sequence that is at least 95% identical over the full length of SEQ ID NO: 6, wherein the amino acid at position 66 is tyrosine, said structural nucleotide sequence being operably linked upstream at the 5' end to a promoter and downstream at the 3' end to a regulatory element.

4. The recombinant DNA construct of claim 3, wherein the promoter is selected from the group consisting of a MADS domain transcription factor, cellulase, polygalacturonase, nopaline synthase (NOS), octopine synthase (OCS), mannopine synthase (mas), cauliflower mosaic virus 19S and 35S (CaMV19S, CaMV35S), enhanced CaMV (eCaMV), ribulose 1,5-bisphosphate carboxylase (ss-RUBISCO), figwort mosaic virus (FMV), CaMV derived AS4, tobacco RB7, wheat POX1, tobacco EIF-4, lectin protein (Lel), and rice RC2 promoter.

5. The recombinant DNA construct of claim 3, wherein said regulatory element comprises an intron.

6. The recombinant DNA construct of claim 5, wherein said intron comprises a hsp70 intron.

7. A recombinant host cell, comprising the recombinant DNA construct of any one of claims 3–6.

8. The recombinant host cell of claim 7 which is a transgenic plant cell.

9. A transgenic plant, comprising the transgenic plant cell of claim 8.

10. A method for preparing a transgenic plant, comprising:
 (a) selecting a host plant cell;
 (b) transforming the host plant cell with a recombinant construct comprising a structural nucleotide sequence;
 (c) obtaining a transformed plant cell; and
 (d) regenerating a transgenic plant from the transformed plant cell,
 wherein the structural nucleotide sequence is a nucleic acid sequence encoding an ethylene receptor protein having an amino acid sequence that is at least 95% identical over the full length of SEQ ID NO: 6, wherein the amino acid at position 66 is tyrosine;
 and wherein said transgenic plant demonstrates reduced abscission of reproductive structures relative to a non-transgenic plant of the same species.

11. The method of claim 10, wherein the transgenic plant is an apple, apricot, pear, plum, blackberry, blueberry, strawberry, cranberry, lemon, maize, wheat, rye, barley, oat, buckwheat, sorghum, rice, sunflower, canola, pea, bean, soybean, cotton, linseed, cauliflower, asparagus, lettuce, tobacco, mustard, sugarbeet, potato, sweet potato, carrot, turnip, celery, tomato, eggplant, cucumber or squash plant.

12. The transgenic plant of claim 9, wherein the transgenic plant is an apple, apricot, pear, plum, blackberry, blueberry, strawberry, cranberry, lemon, maize, wheat, rye, barley, oat, buckwheat, sorghum, rice, sunflower, canola, pea, bean, soybean, cotton, linseed, cauliflower, asparagus, lettuce, tobacco, mustard, sugarbeet, potato, sweet potato, carrot, turnip, celery, tomato, eggplant, cucumber or squash plant.

13. Progeny of the transgenic plant of claim 12 comprising a recombinant DNA construct with a structural nucleotide sequence encoding an ethylene receptor protein having an amino acid sequence that is at least 95% identical over the full length of SEQ ID NO: 6, wherein the amino acid at position 66 is tyrosine.

* * * * *